(12) United States Patent
Richard et al.

(10) Patent No.: US 9,113,951 B2
(45) Date of Patent: Aug. 25, 2015

(54) SEAL ANCHOR FOR USE IN SURGICAL PROCEDURES

(75) Inventors: Paul D. Richard, Shelton, CT (US); Russell Heinrich, Madison, CT (US)

(73) Assignee: Covidien LP, Mansfield, MA (US)

( * ) Notice: Subject to any disclaimer, the term of this patent is extended or adjusted under 35 U.S.C. 154(b) by 834 days.

(21) Appl. No.: 13/400,143

(22) Filed: Feb. 20, 2012

(65) Prior Publication Data

US 2012/0149987 A1 Jun. 14, 2012

Related U.S. Application Data

(63) Continuation of application No. 12/244,024, filed on Oct. 2, 2008, now abandoned.

(60) Provisional application No. 61/075,867, filed on Jun. 26, 2008, provisional application No. 60/997,885, filed on Oct. 5, 2007.

(51) Int. Cl.
*A61B 17/02* (2006.01)
*A61B 17/34* (2006.01)
*A61M 39/02* (2006.01)

(52) U.S. Cl.
CPC ......... *A61B 17/3423* (2013.01); *A61B 17/3431* (2013.01); *A61B 2017/3429* (2013.01); *A61B 2017/3445* (2013.01); *A61B 2017/3447* (2013.01); *A61B 2017/3466* (2013.01); *A61M 2039/0223* (2013.01)

(58) Field of Classification Search
CPC ........... A61B 17/02; A61B 2017/0212; A61B 17/3423; A61B 17/3431

USPC .......................................................... 600/208
See application file for complete search history.

(56) References Cited

U.S. PATENT DOCUMENTS 2,468,985 A * 5/1949 Krotz ............................ 403/225
2,648,985 A 8/1953 Mallory
(Continued)

FOREIGN PATENT DOCUMENTS

| CA | 2702419 | 11/2010 |
|---|---|---|
| EP | 0807416 A | 11/1947 |

(Continued)

OTHER PUBLICATIONS

European Search Report 11194126.6-2310 dated Feb. 5, 2012.
(Continued)

*Primary Examiner* — Christian Sevilla

(57) ABSTRACT

A surgical apparatus for positioning within a tissue tract accessing an underlying body cavity includes a seal anchor member comprising a compressible material and being adapted to transition between a first expanded condition to facilitate securing of the seal anchor member within the tissue tract and in substantial sealed relation with tissue surfaces defining the tissue tract and a second compressed condition to facilitate at least partial insertion of the seal anchor member within the tissue tract. The seal anchor member defines a longitudinal axis, and has leading and trailing ends with at least one longitudinal port extending therebetween adapted for reception of an object whereby compressible material defining the at least one port is adapted to deform to establish a substantial sealed relation with the object. The seal anchor member may comprise a memory foam material and may include a plurality of longitudinal ports.

16 Claims, 17 Drawing Sheets

(56) References Cited

U.S. PATENT DOCUMENTS

| | | |
|---|---|---|
| 3,674,007 A * | 7/1972 | Freis .............. 600/572 |
| 4,402,683 A | 9/1983 | Kopman |
| 5,073,169 A | 12/1991 | Raiken |
| 5,082,005 A | 1/1992 | Kaldany |
| 5,242,415 A | 9/1993 | Kantrowitz et al. |
| 5,295,658 A * | 3/1994 | Atkinson et al. ........ 251/149.1 |
| 5,295,659 A * | 3/1994 | Steele ................ 251/173 |
| 5,312,417 A | 5/1994 | Wilk |
| 5,350,364 A * | 9/1994 | Stephens et al. ........ 604/167.06 |
| 5,366,478 A | 11/1994 | Brinkerhoff et al. |
| 5,375,588 A | 12/1994 | Yoon |
| 5,378,588 A | 1/1995 | Tsuchiya |
| 5,391,156 A | 2/1995 | Hildwein et al. |
| 5,437,683 A | 8/1995 | Neumann et al. |
| 5,443,453 A * | 8/1995 | Walker et al. ........ 604/248 |
| 5,480,410 A | 1/1996 | Cuschieri et al. |
| 5,514,133 A | 5/1996 | Golub et al. |
| 5,524,644 A | 6/1996 | Crook |
| 5,545,179 A | 8/1996 | Williamson, IV |
| 5,556,387 A * | 9/1996 | Mollenauer et al. ........ 604/249 |
| 5,584,850 A * | 12/1996 | Hart et al. .............. 606/185 |
| 5,634,937 A | 6/1997 | Mollenauer et al. |
| 5,649,550 A | 7/1997 | Crook |
| 5,653,705 A | 8/1997 | de la Torre et al. |
| 5,672,168 A | 9/1997 | de la Torre et al. |
| 5,683,378 A | 11/1997 | Christy |
| 5,728,103 A * | 3/1998 | Picha et al. .............. 606/108 |
| 5,735,791 A * | 4/1998 | Alexander et al. .......... 600/37 |
| 5,741,298 A | 4/1998 | MacLeod |
| 5,782,817 A | 7/1998 | Franzel et al. |
| 5,795,290 A | 8/1998 | Bridges |
| 5,813,409 A | 9/1998 | Leahy et al. |
| 5,842,971 A | 12/1998 | Yoon |
| 5,848,992 A | 12/1998 | Hart et al. |
| 5,865,817 A | 2/1999 | Moenning et al. |
| 5,904,703 A | 5/1999 | Gilson |
| 5,906,577 A | 5/1999 | Beane et al. |
| 5,951,588 A | 9/1999 | Moenning |
| 5,976,174 A | 11/1999 | Ruiz |
| 6,024,736 A | 2/2000 | de la Torre et al. |
| 6,033,426 A | 3/2000 | Kaji |
| 6,033,428 A | 3/2000 | Sardella |
| 6,048,309 A | 4/2000 | Flom et al. |
| 6,110,154 A | 8/2000 | Shimomura et al. |
| 6,142,936 A | 11/2000 | Beane et al. |
| 6,171,282 B1 | 1/2001 | Ragsdale |
| 6,228,063 B1 | 5/2001 | Aboul-Hosn |
| 6,254,534 B1 | 7/2001 | Butler et al. |
| 6,315,770 B1 | 11/2001 | de la Torre et al. |
| 6,382,211 B1 | 5/2002 | Crook |
| 6,423,036 B1 | 7/2002 | Van Huizen |
| 6,440,063 B1 | 8/2002 | Beane et al. |
| 6,450,983 B1 | 9/2002 | Rambo |
| 6,454,783 B1 * | 9/2002 | Piskun ................ 606/185 |
| 6,468,292 B1 | 10/2002 | Mollenauer et al. |
| 6,551,270 B1 * | 4/2003 | Bimbo et al. ........ 604/93.01 |
| 6,558,371 B2 | 5/2003 | Dorn |
| 6,562,022 B2 | 5/2003 | Hoste et al. |
| 6,578,577 B2 | 6/2003 | Boandio et al. |
| 6,582,364 B2 | 6/2003 | Butler et al. |
| 6,589,167 B1 | 7/2003 | Shimomura et al. |
| 6,613,952 B2 | 9/2003 | Rambo |
| 6,623,426 B2 | 9/2003 | Bonadio et al. |
| 6,676,639 B1 | 1/2004 | Ternström |
| 6,723,088 B2 | 4/2004 | Gaskill, III et al. |
| 6,811,546 B1 | 11/2004 | Callas et al. |
| 6,814,078 B2 | 11/2004 | Crook |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 7,008,377 B2 | 3/2006 | Beane et al. |
| 7,011,645 B2 | 3/2006 | McGuckin, Jr. et al. |
| 7,033,319 B2 | 4/2006 | Pulford et al. |
| 7,052,454 B2 | 5/2006 | Taylor |
| 7,081,089 B2 | 7/2006 | Bonadio et al. |
| 7,083,626 B2 | 8/2006 | Hart et al. |
| 7,101,353 B2 | 9/2006 | Lui et al. |
| 7,153,261 B2 | 12/2006 | Wenchell |
| 7,163,510 B2 | 1/2007 | Kahle et al. |
| 7,195,590 B2 | 3/2007 | Butler et al. |
| 7,214,185 B1 | 5/2007 | Rosney et al. |
| 7,217,277 B2 | 5/2007 | Parihar et al. |
| 7,223,257 B2 * | 5/2007 | Shubayev et al. .......... 604/175 |
| 7,238,154 B2 | 7/2007 | Ewers et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 * | 3/2008 | Piskun ................. 606/185 |
| 7,377,898 B2 | 5/2008 | Ewers et al. |
| 7,393,322 B2 | 7/2008 | Wenchell |
| 7,445,597 B2 | 11/2008 | Butler et al. |
| 7,473,221 B2 | 1/2009 | Ewers et al. |
| 7,481,765 B2 | 1/2009 | Ewers et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,847 B2 | 5/2010 | Smith |
| 7,727,146 B2 | 6/2010 | Albrecht et al. |
| 7,736,306 B2 | 6/2010 | Brustad et al. |
| 7,758,500 B2 | 7/2010 | Boyd et al. |
| 7,766,824 B2 | 8/2010 | Jensen et al. |
| 7,787,963 B2 | 8/2010 | Geistert et al. |
| 7,798,898 B2 | 9/2010 | Luciano, Jr. et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,896,889 B2 | 3/2011 | Mazzocchi et al. |
| 7,909,760 B2 | 3/2011 | Albrecht et al. |
| 7,951,117 B2 * | 5/2011 | Wingardner et al. .... 604/164.09 |
| 8,016,755 B2 * | 9/2011 | Ewers et al. ............ 600/208 |
| 8,157,786 B2 | 4/2012 | Miller et al. |
| 8,187,177 B2 | 5/2012 | Kahle et al. |
| 8,187,178 B2 | 5/2012 | Bonadio et al. |
| 8,226,553 B2 * | 7/2012 | Shelton et al. ............ 600/208 |
| 8,740,904 B2 * | 6/2014 | Stopek ................ 606/64 |
| D712,034 S * | 8/2014 | Richard et al. .......... D24/145 |
| 2002/0183594 A1 | 12/2002 | Beane et al. |
| 2003/0014076 A1 | 1/2003 | Mollenauer et al. |
| 2003/0093104 A1 | 5/2003 | Bonner et al. |
| 2003/0149443 A1 | 8/2003 | Gaskill et al. |
| 2004/0015185 A1 | 1/2004 | Ewers et al. |
| 2004/0049100 A1 | 3/2004 | Butler et al. |
| 2004/0073090 A1 | 4/2004 | Butler et al. |
| 2004/0092795 A1 | 5/2004 | Bonadio et al. |
| 2004/0092796 A1 | 5/2004 | Butler et al. |
| 2004/0111061 A1 | 6/2004 | Curran |
| 2004/0267096 A1 | 12/2004 | Caldwell et al. |
| 2005/0020884 A1 | 1/2005 | Hart et al. |
| 2005/0090716 A1 | 4/2005 | Bonadio et al. |
| 2005/0090717 A1 | 4/2005 | Bonadio et al. |
| 2005/0096695 A1 | 5/2005 | Olich |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0240082 A1 | 10/2005 | Bonadio et al. |
| 2005/0267419 A1 | 12/2005 | Smith |
| 2005/0288558 A1 | 12/2005 | Ewers et al. |
| 2006/0030755 A1 | 2/2006 | Ewers et al. |
| 2006/0071432 A1 | 4/2006 | Staudner |
| 2006/0084842 A1 | 4/2006 | Hart et al. |

(56) References Cited

U.S. PATENT DOCUMENTS

| | | |
|---|---|---|
| 2006/0129165 A1 | 6/2006 | Edoga et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0241651 A1* | 10/2006 | Wilk .................... 606/108 |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh, II et al. |
| 2006/0270911 A1 | 11/2006 | Voegele et al. |
| 2007/0088202 A1 | 4/2007 | Albrecht et al. |
| 2007/0088204 A1 | 4/2007 | Albrecht et al. |
| 2007/0088241 A1 | 4/2007 | Brustad et al. |
| 2007/0093695 A1 | 4/2007 | Bonadio et al. |
| 2007/0118175 A1 | 5/2007 | Butler et al. |
| 2007/0149859 A1 | 6/2007 | Albrecht et al. |
| 2007/0151566 A1 | 7/2007 | Kahle et al. |
| 2007/0156023 A1 | 7/2007 | Frasier et al. |
| 2007/0185387 A1 | 8/2007 | Albrecht et al. |
| 2007/0203398 A1 | 8/2007 | Bonadio et al. |
| 2007/0208312 A1* | 9/2007 | Norton et al. .................. 604/284 |
| 2007/0225569 A1 | 9/2007 | Ewers et al. |
| 2007/0270654 A1 | 11/2007 | Pignato et al. |
| 2007/0270882 A1 | 11/2007 | Hjelle et al. |
| 2008/0027476 A1 | 1/2008 | Piskun |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0161826 A1 | 7/2008 | Guiraudon |
| 2008/0200767 A1 | 8/2008 | Ewers et al. |
| 2008/0255519 A1* | 10/2008 | Piskun et al. .................. 604/174 |
| 2008/0319261 A1 | 12/2008 | Lucini |
| 2009/0012477 A1 | 1/2009 | Norton et al. |
| 2009/0036745 A1 | 2/2009 | Bonadio et al. |
| 2009/0093752 A1 | 4/2009 | Richard et al. |
| 2009/0093850 A1 | 4/2009 | Richard |
| 2009/0131751 A1 | 5/2009 | Spivey et al. |
| 2009/0137879 A1 | 5/2009 | Ewers et al. |
| 2009/0187079 A1 | 7/2009 | Albrecht et al. |
| 2009/0221968 A1 | 9/2009 | Morrison et al. |
| 2009/0227843 A1 | 9/2009 | Smith et al. |
| 2009/0326330 A1 | 12/2009 | Bonadio et al. |
| 2009/0326332 A1 | 12/2009 | Carter |
| 2010/0063452 A1 | 3/2010 | Edelman et al. |
| 2010/0280326 A1 | 11/2010 | Hess et al. |
| 2010/0298646 A1* | 11/2010 | Stellon et al. .................. 600/208 |
| 2011/0054260 A1 | 3/2011 | Albrecht et al. |

FOREIGN PATENT DOCUMENTS

| | | |
|---|---|---|
| EP | 0950376 | 10/1999 |
| EP | 1312318 | 5/2003 |
| EP | 1774918 A1 | 4/2007 |
| EP | 1932485 A1 | 6/2008 |
| EP | 2226025 | 9/2010 |
| EP | 2229900 | 9/2010 |
| EP | 2253283 | 11/2010 |
| WO | WO 93/14801 | 8/1993 |
| WO | WO96/36283 | 11/1996 |
| WO | WO 97/33520 | 9/1997 |
| WO | WO97/42889 | 11/1997 |
| WO | WO00/32120 A | 6/2000 |
| WO | WO01/08581 | 2/2001 |
| WO | WO01/32116 | 5/2001 |
| WO | WO 01/49363 A1 | 7/2001 |
| WO | WO03/034908 | 5/2003 |
| WO | WO03/071926 | 9/2003 |
| WO | WO2004/043275 | 5/2004 |
| WO | WO2004/054456 | 7/2004 |
| WO | WO2004/075741 | 9/2004 |
| WO | WO2004/075930 | 9/2004 |
| WO | WO2006/019723 | 2/2006 |
| WO | WO2006/100658 | 9/2006 |
| WO | WO2006/110733 | 10/2006 |
| WO | WO2008/015566 | 2/2008 |
| WO | WO2008/042005 | 4/2008 |
| WO | WO 2008/093313 A1 | 8/2008 |
| WO | WO2008/103151 | 8/2008 |
| WO | 2008121294 A1 | 10/2008 |
| WO | WO 2008/121294 | 10/2008 |
| WO | WO2009/036343 | 3/2009 |
| WO | WO2010/141409 | 12/2010 |

OTHER PUBLICATIONS

European Search Report 11250792.6-2310 dated Feb. 24, 2012.
European Search Report for corresponding EP 10251796 date of mailing is Feb. 4, 2011 (3 pages).
European Search Report for EP10 25 0885—completion date Aug. 18, 2010—which application corresponds to U.S. Appl. No. 12/754,638, filed Apr. 6, 2010.
European Search Report for corresponding EP 08253236 date of mailing is Feb. 10, 2009 (3 pages).

* cited by examiner

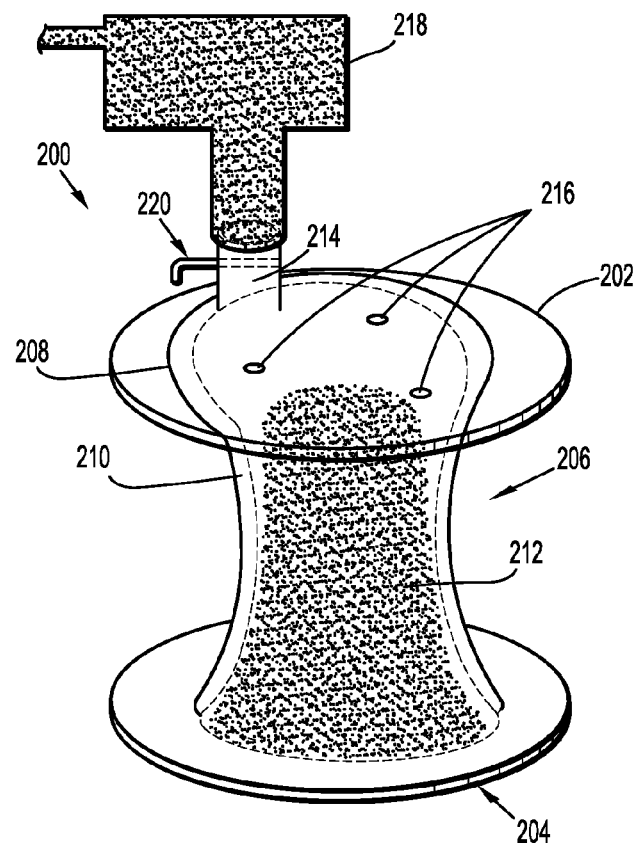
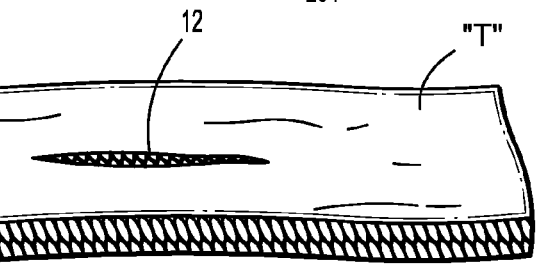
FIG. 7
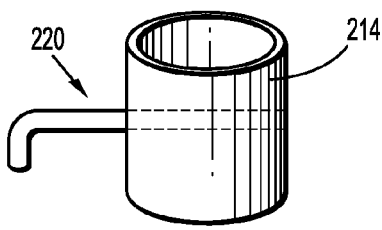
FIG. 7A
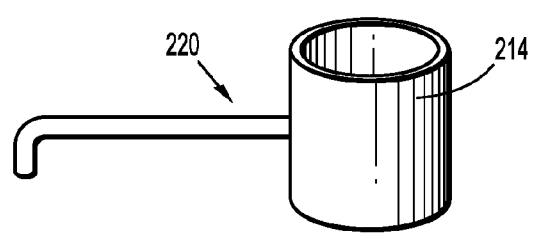
FIG. 7B

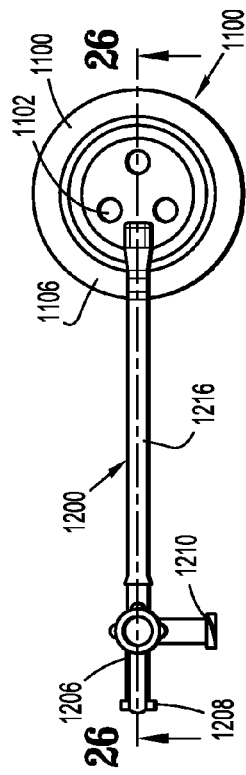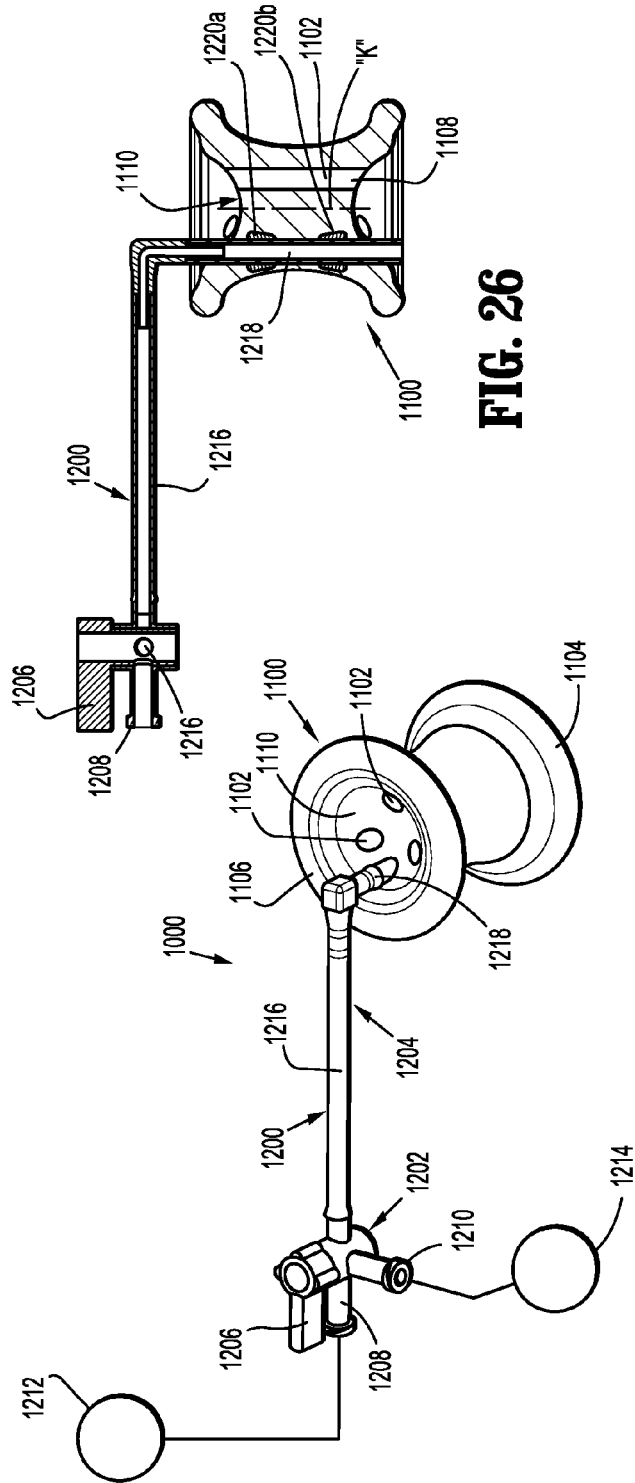

SEAL ANCHOR FOR USE IN SURGICAL PROCEDURES

CROSS REFERENCE TO RELATED APPLICATION

The present application is a continuation of U.S. patent application Ser. No. 12/244,024, filed on Oct. 2, 2008 now abandoned, which claims the benefit of and priority to U.S. Provisional Patent Application Ser. No. 61/075,867, filed Jun. 26, 2008, entitled SEAL ANCHOR FOR USE IN SURGICAL PROCEDURES, and U.S. Provisional Application Ser. No. 60/997,885, filed on Oct. 5, 2007, entitled SEAL ANCHOR FOR USE IN SINGLE INCISION SURGERY, the entire contents of which are incorporated herein by reference.

BACKGROUND

1. Technical Field

The present disclosure relates to a seal for use in a surgical procedure. More particularly, the present disclosure relates to a seal anchor member adapted for insertion into an incision in tissue, and, for the sealed reception of one or more surgical objects such that a substantially fluid-tight seal is formed with both the tissue and the surgical object, or objects.

2. Background of the Related Art

Today, many surgical procedures are performed through small incisions in the skin, as compared to the larger incisions typically required in traditional procedures, in an effort to reduce both trauma to the patient and recovery time. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures.

During a typical minimally invasive procedure, surgical objects, such as surgical access devices, e.g., trocar and cannula assemblies, or endoscopes, are inserted into the patient's body through the incision in tissue. In general, prior to the introduction of the surgical object into the patient's body, insufflation gasses are used to enlarge the area surrounding the target surgical site to create a larger, more accessible work area. Accordingly, the maintenance of a substantially fluid-tight seal is desirable so as to prevent the escape of the insufflation gases and the deflation or collapse of the enlarged surgical site.

To this end, various valves and seals are used during the course of minimally invasive procedures and are widely known in the art. However, a continuing need exists for a seal anchor member that can be inserted directly into the incision in tissue and that can accommodate a variety of surgical objects while maintaining the integrity of an insufflated workspace.

SUMMARY

These and other features of the apparatus disclosed herein will become more readily apparent to those skilled in the art from the following detailed description of various embodiments of the present disclosure. Accordingly, a surgical apparatus for positioning within a tissue tract accessing an underlying body cavity includes a seal anchor member comprising a compressible material and being adapted to transition between a first expanded condition to facilitate securing of the seal anchor member within the tissue tract and in substantial sealed relation with tissue surfaces defining the tissue tract and a second compressed condition to facilitate at least partial insertion of the seal anchor member within the tissue tract. The seal anchor member defines a longitudinal axis, and has leading and trailing ends with at least one longitudinal port extending therebetween.

At least one of the leading and trailing ends of the seal anchor member exhibits an arcuate configuration, which may be either concave or convex. In one embodiment, each of the leading and trailing ends exhibit such an arcuate configuration to facilitate insertion of the seal anchor member within the tissue tract.

The at least one longitudinal port may include a plurality of longitudinal ports which may be configured symmetrically with respect to the longitudinal axis, spaced equidistant from the longitudinal axis, spaced equally from one another, or any combination thereof.

The seal anchor member may be formed of a foam material, which may be at least partially constituted of a material selected from the group consisting of polyisoprene, urethane, and silicone. Alternatively, the seal anchor member may be formed of a gel material.

BRIEF DESCRIPTION OF THE DRAWINGS

Various embodiments of the present disclosure are described hereinbelow with references to the drawings, wherein:

FIG. 7 is a front perspective view of an alternate embodiment of the surgical apparatus of FIG. 1 illustrating a seal anchor member and an inflatable fluid membrane;

FIG. 7A is a front perspective view of the fluid port of the fluid membrane;

FIG. 7B is a front perspective view of the fluid port of FIG. 7A with the valve in an open position.

FIG. 24 illustrates another alternate embodiment of the surgical kit including a seal anchor member and an insufflation/evacuation implement;

FIG. 25 is a top plan view of the seal anchor member and the insufflation/evacuation implement of the surgical kit of FIG. 24;

FIG. 26 is a side cross-sectional view of the seal anchor member and the insufflation/evacuation implement taken along the lines 26-26 of FIG. 25;

DETAILED DESCRIPTION OF THE EMBODIMENTS

Figure 1:
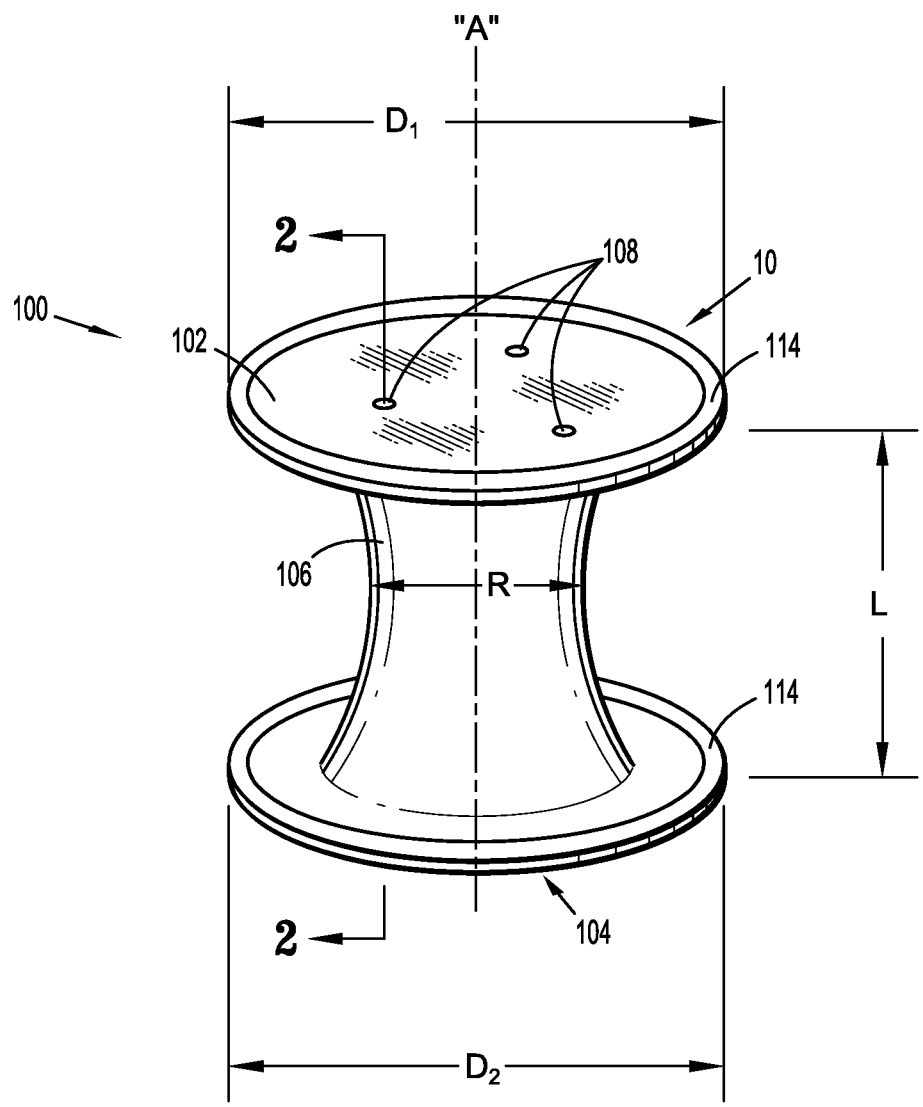
FIG. 1 is a front perspective view of a surgical apparatus in accordance with the principles of the present disclosure shown in an expanded condition illustrating a seal anchor member positioned relative to the tissue.

In the drawings and in the description which follows, in which like references numerals identify similar or identical elements, the term "proximal" will refer to the end of the apparatus which is closest to the clinician during use, while the term "distal" will refer to the end which is furthest from the clinician, as is traditional and known in the art.

Figure 2:
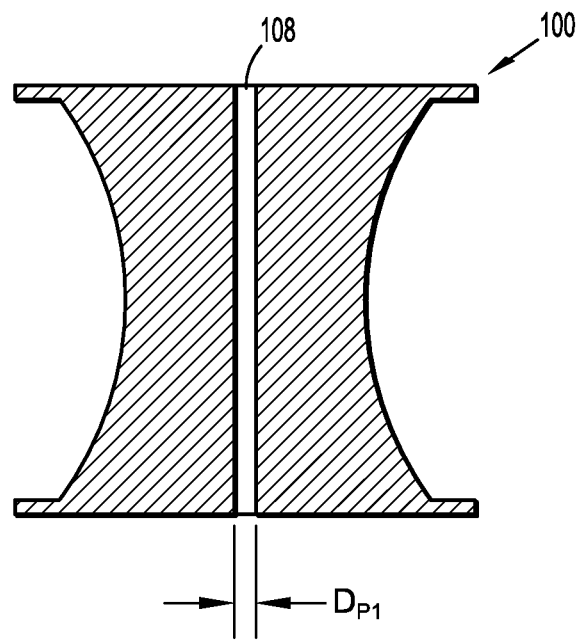
FIG. 2 is a cross-sectional view of the seal anchor member of FIG. 1 taken along line 2-2 of FIG. 1 illustrating a port that extends longitudinally therethrough.
Figure 3:
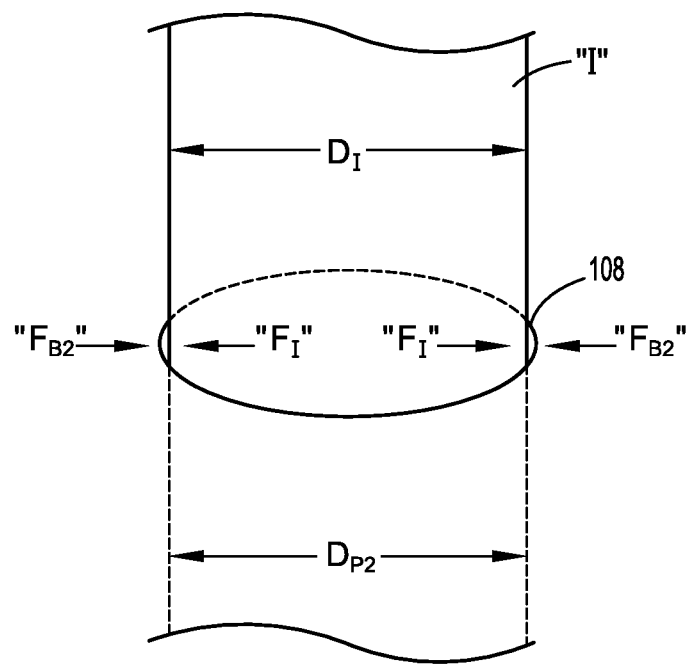
FIG. 3 is a view of the port of FIG. 2 with a surgical object inserted therethrough.

With reference to FIGS. 1-3, a surgical apparatus 10 for use in a surgical procedure, e.g., a minimally invasive procedure is illustrated. Surgical apparatus 10 includes seal anchor member 100 defining a longitudinal axis "A" and having respective trailing (or proximal) and leading (or distal) ends 102, 104 and an intermediate portion 106 disposed between the trailing and leading ends 102, 104. Seal anchor member 100 includes one or more ports 108 that extend longitudinally between trailing and leading ends 102, 104, respectively, and through seal anchor member 100.

Seal anchor member 100 is preferably formed from a suitable foam material having sufficient compliance to form a seal about one or more surgical objects, shown generally as surgical object "I" (FIG. 3), and also establish a sealing relation with the tissue. The foam is preferably sufficiently compliant to accommodate off axis motion of the surgical object "I". In one embodiment, the foam includes a polyisoprene material.

Proximal end 102 of seal anchor member defines a first diameter $D_1$ and distal end 104 defines a second diameter $D_2$. In one embodiment of seal anchor member 100, the respective first and second diameters $D_1$, $D_2$ of the proximal and distal ends 102, 104 are substantially equivalent, as seen in FIG. 1, although an embodiment of seal anchor member 100 in which diameters $D_1$, $D_2$ are different is also within the scope of the present disclosure. As depicted in FIG. 1, proximal and distal ends 102, 104 define substantially planar surfaces. However, embodiments are also contemplated herein in which either or both of proximal and distal ends 102, 104, respectively, define surfaces that are substantially arcuate to assist in the insertion of seal anchor member 100 within a tissue tract 12 defined by tissue surfaces 14 and formed in tissue "T", e.g., an incision, as discussed in further detail below.

Intermediate portion 106 defines a radial dimension "R" and extends longitudinally between proximal and distal ends 102, 104, respectively, to define an axial dimension or length "L". The radial dimension "R" of intermediate portion 106 varies along the axial dimension, or length, "L" thereof. Accordingly, seal anchor member 100 defines a cross-sectional dimension that varies along its length "L", which facilitates the anchoring of seal anchor member 100 within tissue "T", as discussed in further detail below. However, an embodiment of seal anchor member 100 in which the radial dimension "R" remains substantially uniform along the axial dimension "L" thereof is also within the scope of the present disclosure.

The radial dimension "R" of intermediate portion 106 is appreciably less than the respective diameters $D_1$, $D_2$ of proximal and distal ends 102, 104 such that seal anchor member 100 defines an "hour-glass" shape or configuration to assist in anchoring seal anchor member 100 within tissue "T", as discussed in further detail below. However, in an alternate embodiment, the radial dimension "R" of intermediate portion 106 may be substantially equivalent to the respective diameters $D_1$, $D_2$ of proximal and distal ends 102, 104. In cross section, intermediate portion 106 may exhibit any suitable configuration, e.g., substantially circular, oval or oblong.

Each port 108 is configured to removably receive the surgical object "I". Prior to the insertion of surgical object "I", port 108 is in a first state in which port 108 defines a first or initial dimension $D_{P1}$. $D_{P1}$ will generally be about 0 mm such that the escape of insufflation gas (not shown) through port 108 of seal anchor member 100 in the absence of surgical object "I" is substantially prevented. For example, port 108 may be a slit extending the longitudinal length of seal anchor member 100 through proximal and distal ends 102, 104. In the alternative, port 108 may define an opening within seal anchor member 100 having an initial open state. Upon the introduction of surgical object "I", port 108 transitions to a second state in which port 108 defines a second, larger dimension $D_{P2}$ that substantially approximates the diameter $D_I$ of surgical object "I" such that a substantially fluid-tight seal is formed therewith, thereby substantially preventing the escape of insufflation gas (not shown) through port 108 of seal anchor member 100 in the presence of surgical object "I". $D_I$, and thus $D_{P2}$, will generally lie within the range of about 5 mm to about 12 mm, as these dimensions are typical of the surgical objects used during the course of minimally invasive procedures. However, a seal anchor member 100 including a port 108 that is capable of exhibiting substantially larger, or smaller, dimensions in the second state thereof is not beyond the scope of the present disclosure. In addition, seal anchor 100 may be devoid of ports 108. With this arrangement, ports 108 are created within seal anchor member 100 during the insertion of the surgical object "I". In accordance with this embodiment, seal anchor member 100 is formed of a flowable or sufficiently compliable material such as a foam material, e.g., an open-cell polyurethane foam, a thermoplastic elastomer (TPE) or a gel. The formation of seal anchor member 100 may involve a process whereby an inert gas, such as CO2 or nitrogen is infused into the material so as to form a foam structure. Seal anchor member 100 may also be coated with lubricious coating, e.g., Parylene N or C in order to ease insertion of instruments and/or cannulas therethrough.

Figure 4:
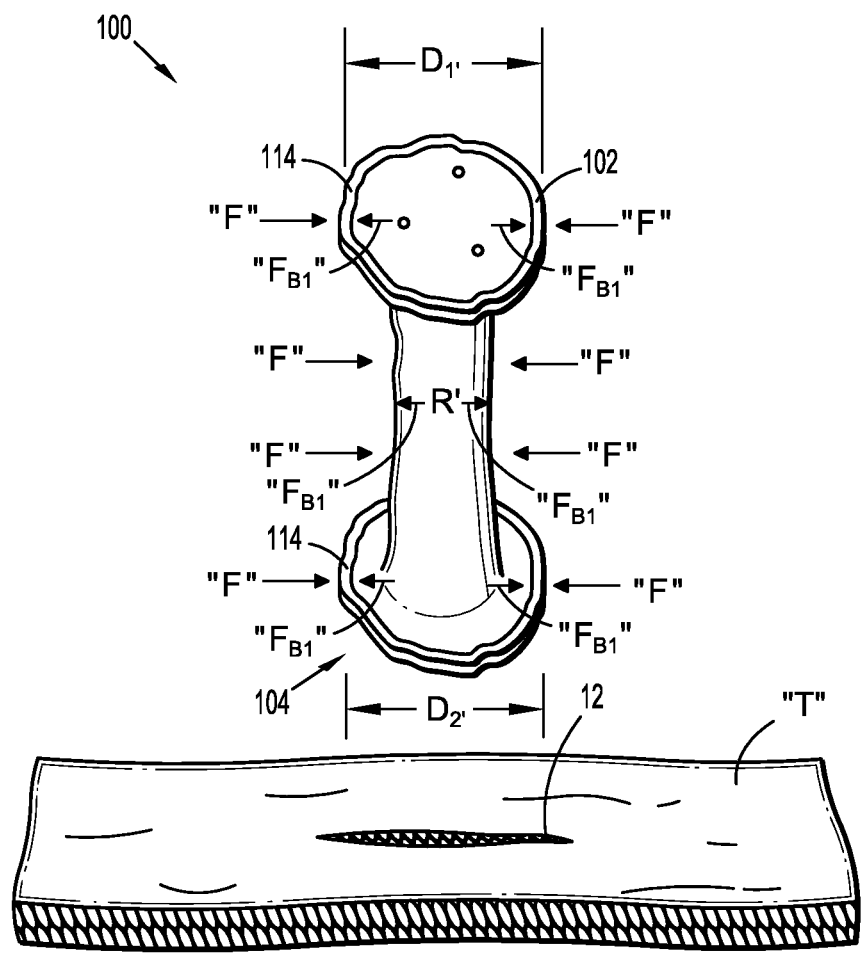
FIG. 4 is a perspective view of the seal anchor member of FIG. 1 shown in a compressed condition and prior to the insertion thereof into an incision in tissue.

Referring now to FIGS. 1 and 4, seal anchor member 100 is adapted to transition from an expanded condition (FIG. 1) to a compressed condition (FIG. 4) so as to facilitate the insertion and securement thereof within tissue tract 12 in tissue "T". In the expanded condition, seal anchor member 100 is at rest and the respective radial dimensions $D_1$, $D_2$ of the proximal and distal ends 102, 104 of seal anchor member 100, as well as the radial dimension R of the intermediate portion 106 are such that the seal anchor member 100 cannot be inserted within tissue tract 12. However, as seen in FIG. 4, in the compressed condition, proximal and distal ends 102, 104 of seal anchor member 100, as well as intermediate portion 106 are dimensioned for insertion into tissue tract 12.

Seal anchor member 100 is formed of a biocompatible compressible material that facilitates the resilient, reciprocal transitioning of seal anchor member 100 between the expanded and compressed conditions thereof. In one embodiment, the compressible material is a "memory" foam. An external force "F" is applied to seal anchor member 100 to cause the seal anchor member 100 to assume the compressed condition. External force "F" is directed inwardly and when seal anchor member 100 is subjected thereto, e.g., when seal anchor member 100 is squeezed, seal anchor member 100 undergoes an appreciable measure of deformation, thereby transitioning into the compressed condition.

As depicted in FIG. 4, as seal anchor member 100 is compressed under the influence of external force "F", an internal biasing force "$F_{B1}$" is created within seal anchor member 100 that is directed outwardly, opposing force "F". Internal biasing force "$F_{B1}$" endeavors to expand seal anchor member 100 and thereby return seal anchor member 100 to the expanded condition thereof. Accordingly, as long as seal anchor member 100 is subject to external force "F", seal anchor member 100 remains in the compressed condition. Upon the removal of external force "F", however, biasing force "$F_{B1}$" acts to return seal anchor member 100 to the expanded condition.

The compressible material comprising seal anchor member 100 also facilitates the resilient transitioning of port 108 between its first closed state (FIGS. 1-2) and its second state (FIG. 3). As previously discussed, prior to the insertion of surgical object "I", port 108 is in its first state in which port 108 defines a first or initial dimension $D_{P1}$. Port 108 may incorporate a slit extending the longitudinal length of seal anchor member 100. In this first state, port 108 is at rest and is not subject to any external forces. However, upon the introduction of surgical object "I" through port 108 as depicted in FIG. 3, the surgical object "I" exerts a force "$F_I$" upon port 108 that is directed radially outward. Force "$F_I$" acts to enlarge the dimensions of port 108 and thereby transition port 108 into the second state thereof in which port 108 defines a second, larger dimension $D_{P2}$ that substantially approximates the diameter $D_I$ of surgical object "I". Consequently, an internal biasing force "$F_{B2}$" is created that is directed radially inward, in opposition to force "$F_I$". Internal biasing force "$F_{B2}$" endeavors to return port 108 to reduce the internal dimension of port 108 and thereby return port 108 to the first state thereof. Internal biasing force "$F_{B2}$" is exerted upon surgical object "I" and acts to create a substantially fluid-tight seal therewith. The significance of forces "$F_{B1}$" and "$F_{B2}$" will be discussed in further detail below.

Referring again to FIG. 1, one or more positioning members 114 may be associated with either or both of trailing (or proximal) end 102 and distal (or leading) end 104 of seal anchor member 100. Positioning members 114 may be composed of any suitable biocompatible material that is at least semi-resilient such that positioning members 114 may be resiliently deformed and may exhibit any suitable configuration, e.g., substantially annular or oval. Prior to the insertion of seal anchor member 100, positioning members 114 are deformed in conjunction with the respective proximal and distal ends 102, 104 of seal anchor member 100 to facilitate the advancement thereof through tissue tract 12 (FIG. 4). Subsequent to the insertion of seal anchor member 100 within tissue tract 12, the resilient nature of positioning members 114 allows positioning members to return to their normal, substantially annular configuration, thereby aiding in the expansion of either or both of the respective proximal and distal ends 102, 104 and facilitating the transition of seal anchor member 100 from its compressed condition to its expanded condition. Positioning members 114 also may engage the walls defining the body cavity to further facilitate securement of seal anchor member 100 within the body tissue. For example, positioning member 114 at leading end 104 may engage the internal peritoneal wall and positioning member 114 adjacent trailing end 102 may engage the outer epidermal tissue adjacent the incision 12 within tissue "T". In another embodiment of seal anchor member 100, one or more additional positioning members 114 may be associated with intermediate portion 106.

The use and function of seal anchor member 100 will be discussed during the course of a typical minimally invasive procedure. Initially, the peritoneal cavity (not shown) is insufflated with a suitable biocompatible gas such as, e.g., $CO_2$ gas, such that the cavity wall is raised and lifted away from the internal organs and tissue housed therein, providing greater access thereto. The insufflation may be performed with an insufflation needle or similar device, as is conventional in the art. Either prior or subsequent to insufflation, a tissue tract 12 is created in tissue "T", the dimensions of which may be varied dependent upon the nature of the procedure.

Figure 5:
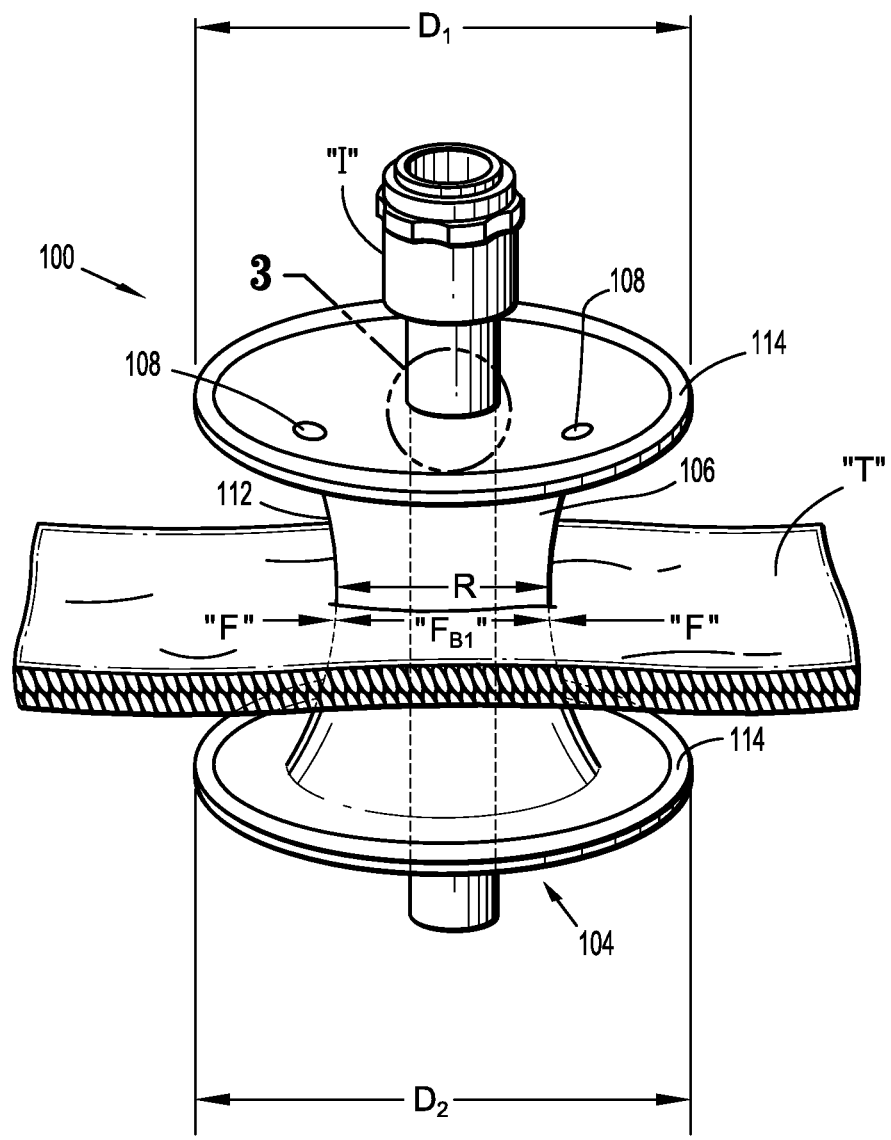
FIG. 5 is a front perspective view of the seal anchor member shown in the expanded condition and subsequent to its insertion into the incision.

Prior to the insertion of seal anchor member 100 within tissue tract 12, seal anchor member 100 is in its expanded condition in which the dimensions thereof prohibit the insertion of seal anchor member 100 into tissue tract 12. To facilitate insertion, the clinician transitions seal anchor member 100 into the compressed condition by applying a force "F" thereto, e.g., by squeezing seal anchor member 100. Force "F" acts to reduce the radial dimensions of the proximal and distal ends 102, 104, respectively, to $D_1'$ and $D_2'$ (FIG. 4) including positioning members 114 (if provided) and to reduce the radial dimension of intermediate portion 106 to R' such that seal anchor member 100 may be inserted into tissue tract 12. As best depicted in FIG. 5, subsequent to its insertion, distal end 104, positioning member 114 (if provided) and at least a section 112 of intermediate portion 106 are disposed beneath the tissue "T". Seal anchor member 100 is caused to transition from the compressed condition to the expanded condition by removing force "F" therefrom.

During the transition from the compressed condition to the expanded condition, the dimensions of seal anchor member 100, i.e., the respective radial dimensions $D_1'$, $D_2'$ (FIG. 4) of the proximal and distal ends 102, 104 are increased to $D_1$ and $D_2$ (FIG. 5) and the radial dimension R' is increased to R. The expansion of distal end 104 is relatively uninhibited given the disposition thereof beneath tissue "T", and accordingly, distal end 104 is permitted to expand substantially, if not completely. However, as seen in FIG. 5, the expansion of the section 112 of the intermediate portion 106 is limited by the tissue surfaces 14 (FIG. 1) defining tissue tract 12, thereby subjecting intermediate portion 106 to an external force "F" that is directed inwardly. As discussed above, this creates an internal biasing force "$F_{B1}$" that is directed outwardly and exerted upon tissue surfaces 14, thereby creating a substantially fluid-tight seal between the seal anchor member 100 and tissue surfaces 14 and substantially preventing the escape of insufflation gas around seal anchor member 100 and through tissue tract 12.

In the expanded condition, the respective radial dimensions $D_1$, $D_2$ of the proximal and distal ends 102, 104 are substantially larger than the radial dimension R of the intermediate portion 106 thereby giving seal anchor member 100 the aforedescribed "hour-glass" configuration. Subsequent to insertion, the radial dimension $D_2$ of distal end 104 and positioning member 114 is also substantially larger than the dimensions of the tissue tract 12. Consequently, seal anchor member 100 may not be removed from tissue tract 12 in the expanded condition and thus, seal anchor member 100 will remain anchored within the tissue "T" until it is returned to its compressed condition.

After successfully anchoring seal anchor member 100 within the patient's tissue "T", one or more surgical objects "I" may be inserted through ports 108. FIG. 5 illustrates a surgical object "I" introduced through one of ports 108. As previously discussed, prior to the insertion of surgical object "I", port 108 is in its first state in which port 108 defines an initial dimension $D_{P1}$ which may be negligible in that port 108, in one embodiment, is a longitudinal slit. Accordingly, prior to the escape of insufflation gas through port 108, in the absence of surgical object "I" is minimal, thereby preserving the integrity of the insufflated workspace.

Figure 6:
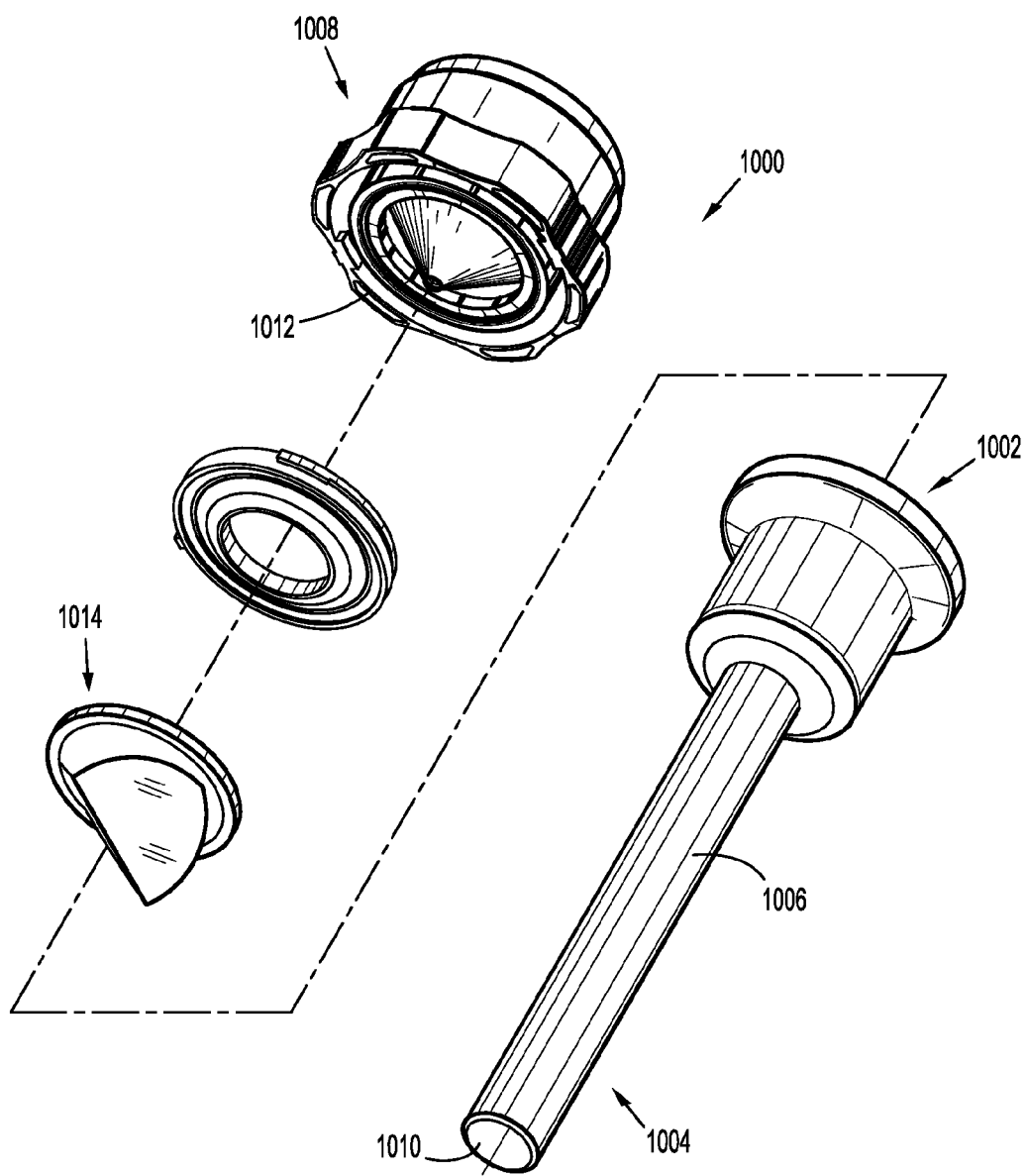
FIG. 6 is an exploded perspective view of an exemplary cannula for insertion within the longitudinal extending port of the seal anchor member.

Surgical object "I" may be any suitable surgical instrument and, accordingly, may vary in size. Suitable surgical objects to be introduced within one or more of the ports 108 include minimally invasive grasper instruments, forceps, clip-appliers, staplers, etc. It is further contemplated that the surgical objects may include a conventional cannula 1000 as depicted in FIG. 6. Cannula 1000 is configured for removable insertion into port 108 and includes respective proximal and distal ends 1002, 1004, a shaft or elongate member 1006 disposed therebetween and seal housing 1008. Elongate member 1006 defines an opening 1010 extending longitudinally therethrough that is dimensioned to permit the passage of surgical instrumentation (not shown), such as an obturator. Disposed within seal housing 1008 is an instrument seal 1012 that is adapted to receive the surgical instrumentation inserted into longitudinal opening 1010 so as to form a substantially fluid-tight seal therewith. Cannula 1000 further includes a closure valve 1014 that is biased into a closed position, but is adapted to open upon the introduction of the surgical instrumentation inserted into longitudinal opening 1010 to allow the surgical instrumentation to pass therethrough. In the closed position, i.e., in the absence of surgical instrumentation, closure valve 1014 prevents the communication of insufflation gas therethrough.

Upon the introduction of surgical object "I", e.g., cannula 1000, port 108 is enlarged, thereby transitioning into its second state in which port 108 defines a second dimension $D_{P2}$ (FIG. 3) that substantially approximates the diameter $D_I$ of surgical object "I", thereby creating a substantially fluid tight seal with surgical object "I" and substantially preventing the escape of insufflation gas (not shown) through port 108 of seal anchor member 100 in the presence of a surgical object "I", as previously discussed.

Figure 8:
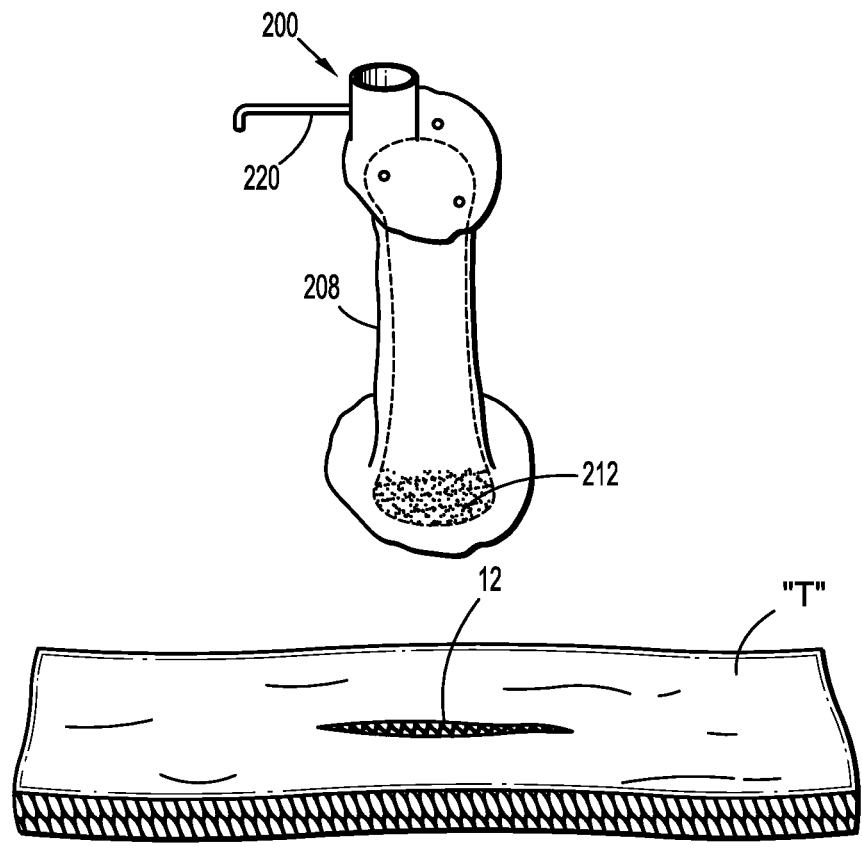
FIG. 8 is a front perspective view of the seal anchor member of the surgical apparatus of in compressed condition prior to the insertion within the incision.
Figure 9:
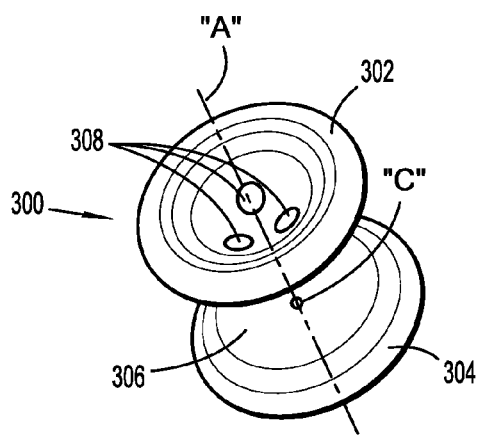
FIG. 9 is a top perspective view of an alternate embodiment of the seal anchor member of FIG. 1 having concave proximal and distal portions.
Figure 10:
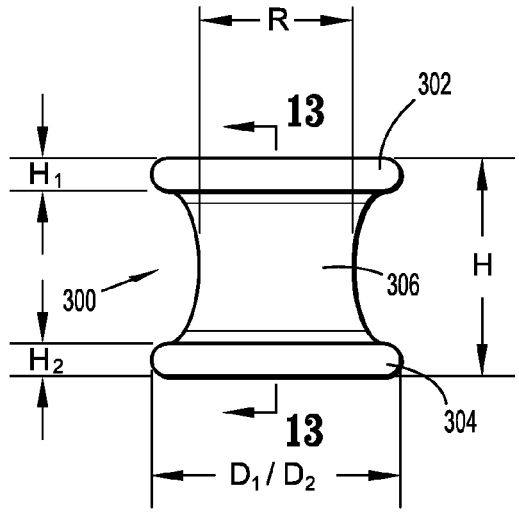
FIG. 10 is a side view of the seal anchor member of FIG. 9.
Figure 11:
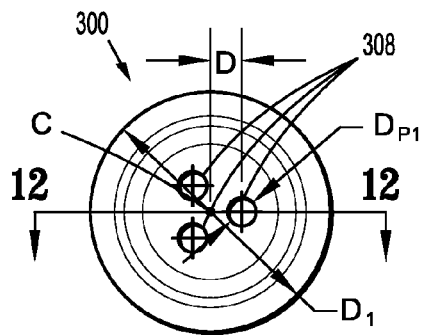
FIG. 11 is a top view of the seal anchor member of FIG. 9.
Figure 12:
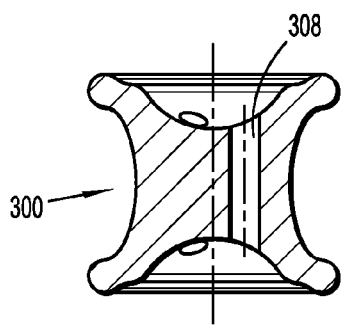
FIG. 12 is a cross-sectional view of the seal anchor member of FIG. 9 taken along line 12-12 of FIG. 11 illustrating a port that extends longitudinally therethrough.
Figure 13:
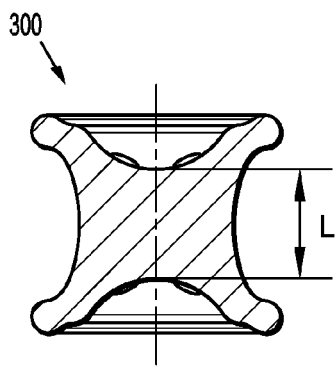
FIG. 13 is a cross-sectional view of the seal anchor member of FIG. 9 taken along line 13-13 of FIG. 10.

Referring now to FIGS. 7-8, an alternate embodiment of a seal anchor member 200 is disclosed. Seal anchor member 200 comprises a resilient conformable material such as foam or, alternatively, a gel. Seal anchor member 200, proximal and distal ends 202, 204, and an intermediate portion 206 disposed therebetween. Seal anchor member 200 further includes expandable membrane 208 defining internal cavity 210. Membrane 208 may be, e.g., substantially annular or donut-shaped in configuration, although any conceivable shape may be employed, and may be secured, attached or embedded to or within the foam or gel material of seal anchor member 200. In one embodiment, membrane 208 surrounds foam or gel segment 212 thereby defining the periphery of seal anchor member 200. One or more fluid ports 214 are in communication with internal cavity 210 of membrane 208 and one or more longitudinal ports 216 that extend through foam segment 212 of seal anchor member 200.

Internal cavity 210 defined by membrane 208 is configured to retain a fluid therein. Membrane 208 may be formed of any suitable biocompatible that is sufficiently resilient to allow the flow of fluid into and out of internal cavity 210 to cause the expansion and contraction thereof. In addition, the material comprising membrane 208 is substantially impermeable with respect to the fluid to ensure that the flow of fluid into and out of internal cavity occurs solely through fluid port 214.

Fluid port 214 is adapted for connection to a fluid source 218. Fluid port 214 may be any member or structure suitable for this intended purpose. Although depicted as including a single fluid port 214, in alternate embodiments, seal anchor member 200 may include additional fluid ports, e.g., on each of proximal and distal ends 202, 204, respectively. Fluid port 214 may also include a valve 220 that is selectively positionable between an open position (FIG. 7A) and a closed position (FIG. 7B) to regulate the flow of fluid into and out of internal cavity 210 through fluid port 214.

As with seal anchor member 100 discussed above with respect to FIGS. 1-6, seal anchor member 200 is adapted to transition from an expanded condition (FIG. 7) to a compressed condition (FIG. 8). In the compressed condition (FIG. 8), seal anchor member 200 is configured for insertion within tissue tract 12 in tissue "T", in a similar manner, as discussed above with respect to seal anchor member 100 (FIGS. 1-5). Seal anchor member 200 is positioned within tissue "T" whereby foam segment 212 of the seal anchor member 200 and assumes the expanded condition. Fluid port 214 may be connected to fluid source 216 (FIG. 7) and fluid is communicated into the internal cavity 210 defined by membrane 208. As internal cavity 210 fills with fluid, the dimensions of internal cavity 210 and membrane 208 are enlarged, thereby forcing the outer surface of seal anchor member 200 outwardly and establishing a seal within the incision "I".

With reference now to FIGS. 9-13, another embodiment of a seal anchor member 300 is disclosed. Seal anchor member 300 extends along a longitudinal axis "A" that passes through a centerpoint "C" thereof. Seal anchor member 300 defines an overall axial dimension "H" measured along the longitudinal axis "A". The overall axial dimension "H" will generally lay substantially within the range of approximately 25 mm to approximately 75 mm, and desirably, is approximately equal to 50 mm. However, the present disclosure also contemplates a seal anchor member 300 that defines either a substantially larger or smaller overall axial dimension "H".

As with each of the previous embodiments, the material comprising seal anchor member 300 is sufficiently compliant to accommodate off-axis movement of the surgical object, or objects, "I" inserted therethrough that may be necessitated during the course of the minimally invasive surgical procedure in which seal anchor member 300 is employed. In one embodiment, seal anchor member 300 is formed from a suitable foam material, which may be at least partially constituted of polyisoprene, urethane, or silicone, or the like. Alternatively, seal anchor member 300 may be formed of a biocompatible gel material.

As with the previous embodiments, seal anchor member 300 includes respective trailing (or proximal) and leading (or distal) ends 302, 304, an intermediate portion 306 disposed therebetween, and one or more ports 308 that extend longitudinally between the respective trailing and leading ends 302, 304 and through seal anchor member 300.

Proximal end 302 of seal anchor member 300 defines a first radial dimension $D_1$ and a first axial dimension $H_1$, and distal end 304 defines a second radial dimension $D_2$ and a second axial dimension $H_2$. The present disclosure contemplates a seal anchor member 300 having proximal and distal ends 302, 304 that define radial dimensions $D_1$, $D_2$ generally laying substantially within the range of approximately 25 mm to approximately 75 mm, and axial dimensions $H_1$, $H_2$ generally laying substantially within the range of approximately 6 mm to approximately 11 mm, respectively. Desirably, however, seal anchor member 300 includes proximal and distal ends 302, 304 having radial dimensions $D_1$, $D_2$ that are approximately equal to 50 mm and axial dimensions $H_1$, $H_2$ that are approximately equal to 8.5 mm, respectively. A seal anchor member 300 having proximal and distal ends 102, 104 that define substantially larger or smaller radial and axial dimensions is also within the scope of the present disclosure.

In the embodiment illustrated in FIGS. 9-13, seal anchor member 300 includes respective proximal and distal ends 302, 304 having respective first and second radial dimensions $D_1$, $D_2$ that are substantially equivalent. However, an embodiment of seal anchor member 300 that includes respective proximal and distal ends 302, 304 having respective first and second radial dimensions $D_1$, $D_2$ that differ is also contemplated herein.

Intermediate portion 306 of seal member 300 defines a radial dimensions "R" generally laying substantially within the range of approximately 20 mm to approximately 50 mm, and an axial dimension "L" generally laying substantially within the range of approximately 10 mm to approximately 40 mm. While it is desirable for the radial and axial dimensions "R", "L" of intermediate portion 306 to be approximately equal to 35 mm and 25 mm, respectively, a seal anchor member 300 having an intermediate portion 306 that defines substantially larger or smaller radial and axial dimensions is not beyond the scope of the present disclosure. The radial dimension "R" of intermediate portion 306 may be substantially uniform or variable along the axial dimension "L" thereof, and may be appreciably less than, greater than, or equal to the respective radial dimensions $D_1$, $D_2$ of proximal and distal ends 302, 304, as discussed above.

As with each of the previous embodiments, the port, or ports, 308 are configured to removably receive a surgical object "I" (not show), and prior to the insertion of surgical object "I", each port 308 defines an initial dimension $D_{P1}$. $D_{P1}$ will generally lie substantially within the range of approximately 0 mm to approximately 13 mm, and desirably, is approximately equal to 6.5 mm. However, a seal anchor member 300 having a port 308 that defines a substantially greater initial dimension $D_{P1}$ is not beyond the scope of the present disclosure. In those embodiments of seal member 300 employing a port 308 that defines an initial dimension $D_{P1}$ approximately equal to 0 mm, the escape of insufflation gas (not shown) therethrough may be substantially prevented in the absence of surgical object "I".

Seal anchor member 300 may include a plurality of ports 308 that are symmetrically arranged with respect to the longitudinal axis "A". It is further contemplated that each port 308 may be spaced equidistant from the longitudinal axis "A". In one embodiment, each port 308 is spaced a distance "D" from the longitudinal axis "A" generally laying substantially within the range of approximately 6 mm to approximately 11 mm, and desirably, approximately equal to 8.5 mm. However, in alternate embodiments, seal anchor member 300 may include ports 308 spaced either a larger or smaller distance from the longitudinal axis "A". Ports 308 may be arranged such that they are spaced equally from one another, or alternatively, the distance between adjacent ports 308 may vary.

Figure 14:
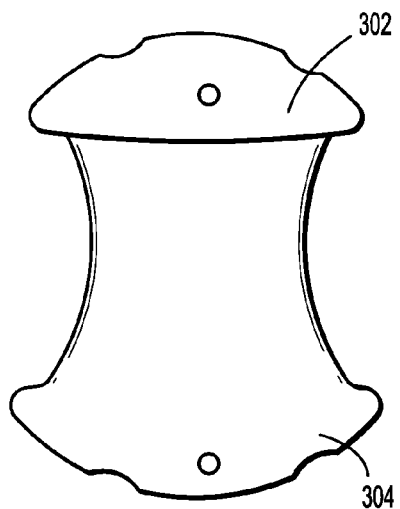
FIG. 14 is a front perspective view of another embodiment of the seal anchor member of FIG. 1 having convex proximal and distal portions.

Either or both of the respective proximal and distal ends 302, 304 of seal anchor member 300 define surfaces that are substantially arcuate, e.g., concave, as seen in FIGS. 9-13, to facilitate insertion of seal anchor member 300 within a tissue tract 12 (FIG. 1) defined by tissue surfaces 14 and formed in tissue "T", e.g., an incision, as discussed above. The concave orientation may, e.g., assist in guiding a surgical instrument toward one of ports 308 and also confine the tip of the instrument within the outer boundary of the proximal end 302 of seal anchor member 300. In the alternative, either or both of proximal and distal ends 302, 304 may be convex as seen in FIG. 14.

Figure 15:
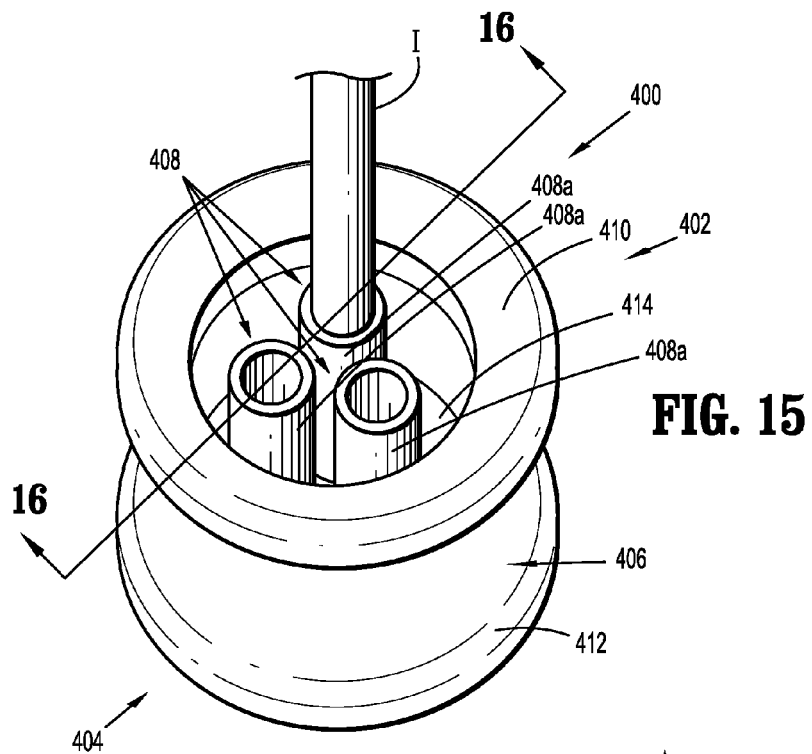
FIG. 15 is a top, perspective view of yet another embodiment of the seal anchor member of FIG. 1 shown in an expanded condition with a surgical object inserted into one of the ports extending longitudinally therethrough.
Figure 16:
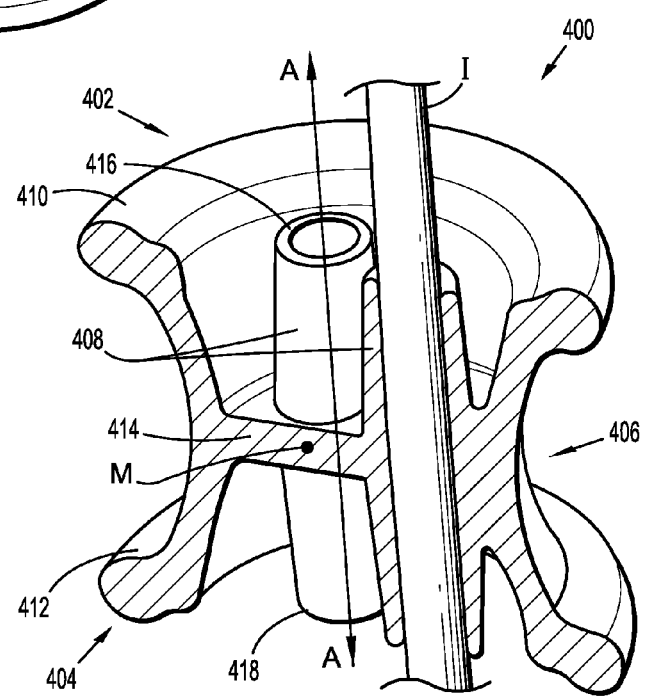
FIG. 16 is a perspective, cross-sectional view of the seal anchor member of FIG. 15 taken along line 16-16.

Referring now to FIGS. 15-16, another embodiment of seal anchor member 400 is disclosed. Seal anchor member 400 includes respective proximal and distal ends 402, 404, an intermediate portion 406 disposed between the proximal and distal ends 402, 404, and one or more generally tubular port segments 408 defining ports 408a that extend longitudinally through seal anchor member 400 and between the proximal and distal ends 402, 404. The seal anchor member 400 is substantially similar to the seal anchor 100 illustrated in FIGS. 1-5, and accordingly, will only be discussed with respect to its differences.

In one embodiment, as seen in FIGS. 15-16, seal anchor member 400 defines corresponding proximal and distal rims 410, 412, respectively. The proximal and distal rims 410, 412 facilitate deformation of seal anchor member 400 from the expanded condition (FIGS. 15-16) to the compressed condition (not shown) and the anchoring of seal anchor member 400 within tissue, as previously discussed with respect to the seal anchor member 100 illustrated in FIGS. 1-5.

Tubular port segments 408 are secured to the intermediate portion 406 by a connective member 414 such that the longitudinal position of the port segments 408 remain substantially constant with respect to the respective proximal and distal rims 410, 412 during insertion and removal of the surgical object "I". In the embodiment illustrated in FIGS. 15-16, the connective member 414 extends inwardly from the intermediate portion 406 and is attached to ports 408 at midpoints "M" thereof that are spaced equidistant from the respective proximal and distal rims 410, 412. In various embodiments, the connective member 414 may be composed of the same material comprising the seal anchor member 400, or alternatively, the connective member 414 may be composed of a material that is substantially more rigid, to inhibit off-axis movement of the surgical object "I" following its insertion into one of the ports 408, or substantially less rigid, to facilitate off-axis movement of the surgical object "I".

In the embodiment illustrated in FIGS. 15-16, the ports 408 extend longitudinally along the longitudinal axis "A" defined by the seal anchor member 400 such that a proximal end 416 of the ports 408 is coplanar with the proximal rim 402 and a distal end 418 of the ports 408 is coplanar with the distal rim 404. However, embodiments in which the proximal and distal ends 416, 418 of ports 408 extend beyond the proximal and distal rims 402, 404, respectively, such that they extend at least partially from the intermediate portion 406, and embodiments in which the proximal and distal ends 416, 418 of ports 408 are defined entirely within the intermediate portion 406 are also contemplated herein.

Figure 18:
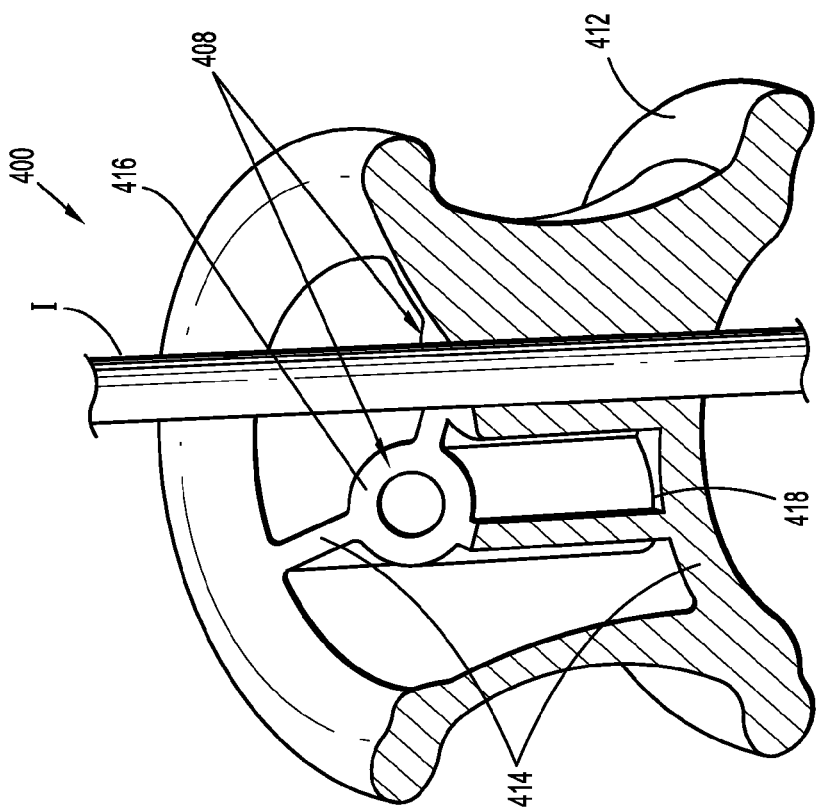
FIG. 18 is a perspective, cross-sectional view of the seal anchor member of FIG. 17 taken along line 18-18.
Figure 17:
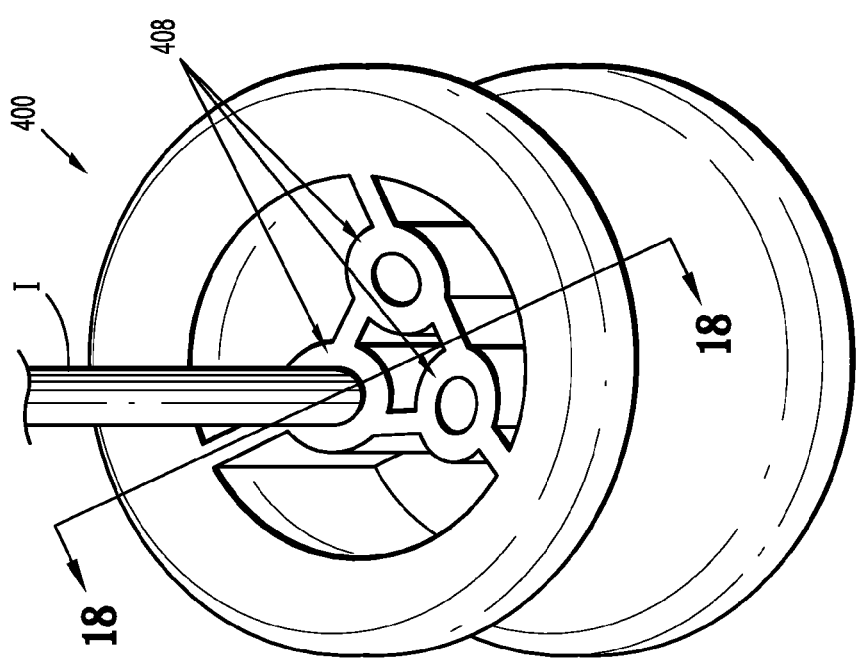
FIG. 17 is a top, perspective view of still another embodiment of the seal anchor member of FIG. 1 shown in an expanded condition with a surgical object inserted into one of the ports extending longitudinally therethrough.

Referring now to FIGS. 17-18, in an alternate embodiment, the connective member 414 extends inwardly from the distal rim 412 and is attached to ports 408 at the distal ends 418 thereof. To further limit off-axis movement of the surgical object "I" upon insertion, the connective member 414 may extend substantially along the length of the ports 408, as illustrated. Either or both of the respective proximal and distal ends 416, 418 of the ports 408 may be beveled, e.g., to facilitate the insertion and removal of the surgical object "I".

Figure 19:
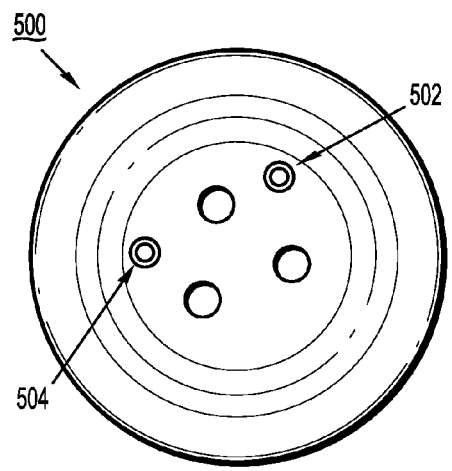
FIG. 19 is a top view of an alternate embodiment of the seal anchor member seen in FIG. 1 including an ingress port and an egress port each extending longitudinally therethrough.
Figure 20:
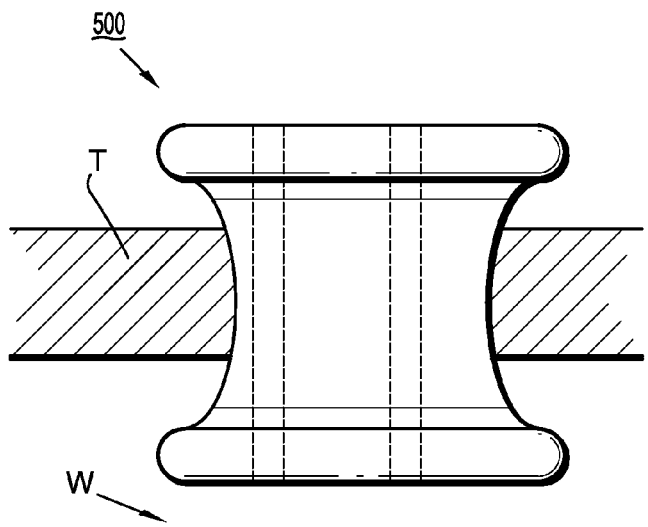
FIG. 20 is a side, cross-sectional view of the seal anchor member of FIG. 19 positioned within a patient's tissue.

FIGS. 19-20 illustrate an alternate embodiment of the seal anchor member, referred to generally by reference number 500. The seal anchor member 500 is substantially similar to the seal anchor member 300 discussed above with respect to FIGS. 9-14, and accordingly, will only be discussed with respect to its differences therefrom.

Figure 21:
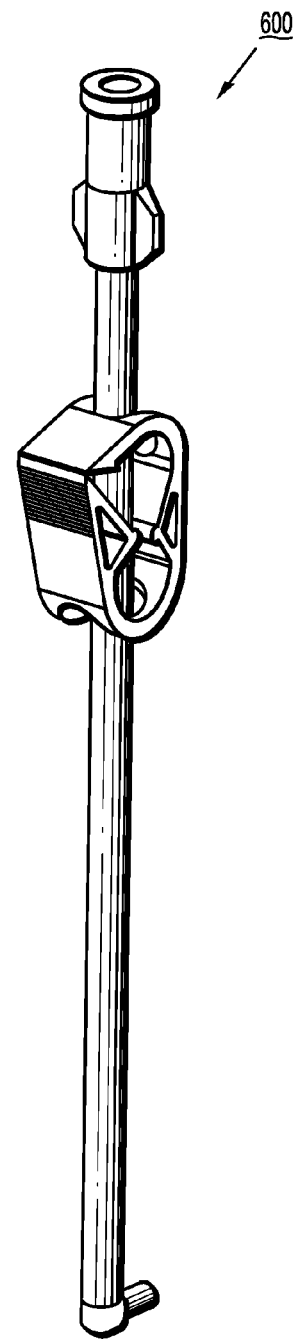
FIG. 21 is a side, perspective view of a tube assembly for insertion into the ingress port of one embodiment of the seal anchor member of FIG. 19.

The seal anchor member 500 includes an ingress port 502 and an egress port 504 extending longitudinally through the seal anchor member 500. The ingress port 502 facilitates the communication of a fluid through the seal anchor member 500 and into a surgical worksite "W" located beneath the patient's tissue "T". In one embodiment, the ingress port 502 is configured and dimensioned to removably receive a tube assembly 600 (FIG. 21) to facilitate insufflation of the surgical worksite "W". In contrast, the egress port 504 facilitates the communication of a fluid, such as smoke, through the seal anchor member 500 and out of the surgical worksite "W". To substantially limit the communication of fluid into and out of the surgical worksite "W", the ingress and egress ports 502, 504 may respectively include a one-way valve (not shown), such as a duck-bill or zero closure valve. Alternatively, the ingress port 502 and the egress port 504 may be normally biased towards a closed condition.

Figure 22:
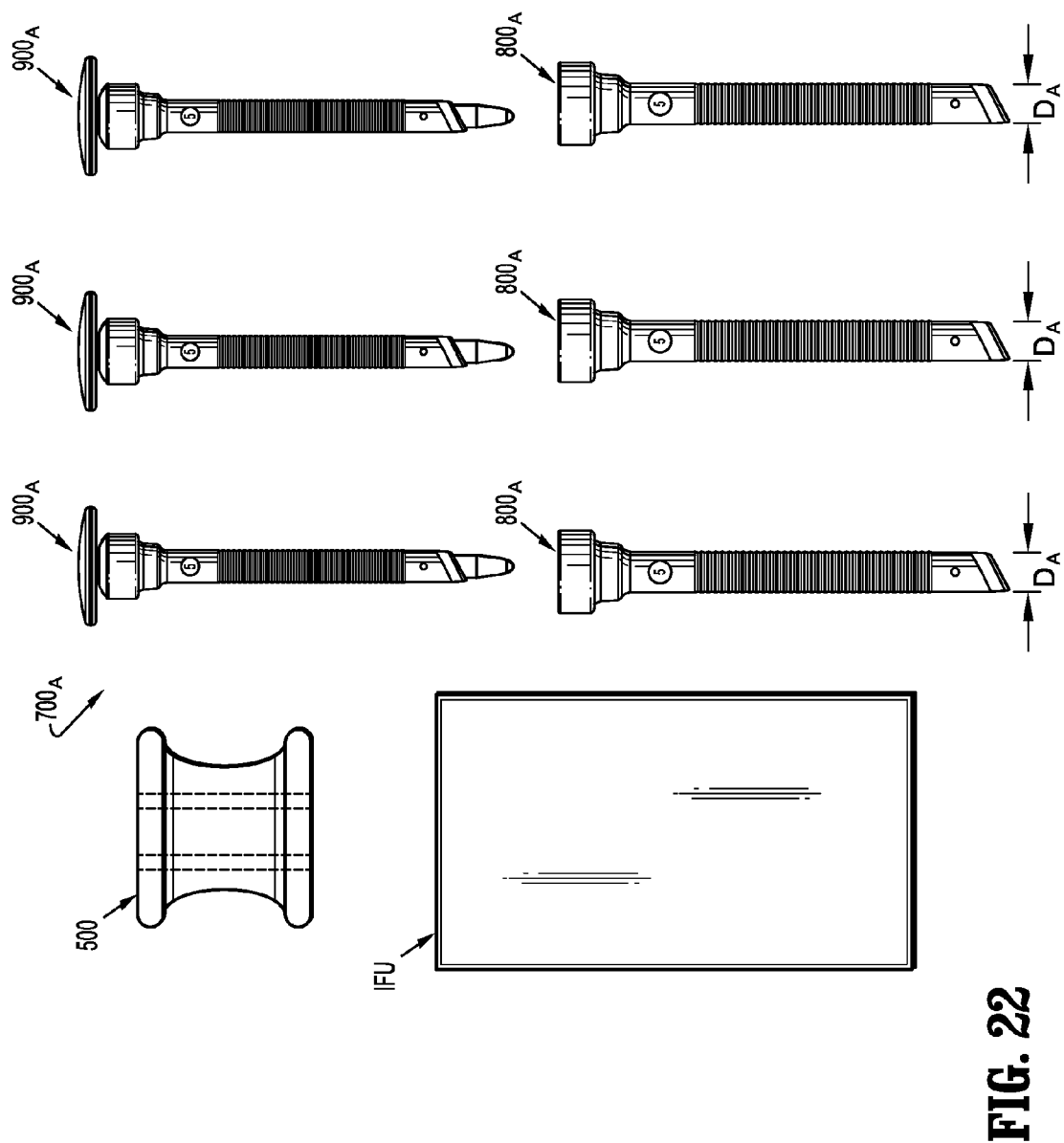
FIG. 22 illustrates a first kit in accordance with the principles of the present disclosure including the seal anchor member of FIG. 19 and a plurality of obturators positionable within a plurality of cannulae.
Figure 23:
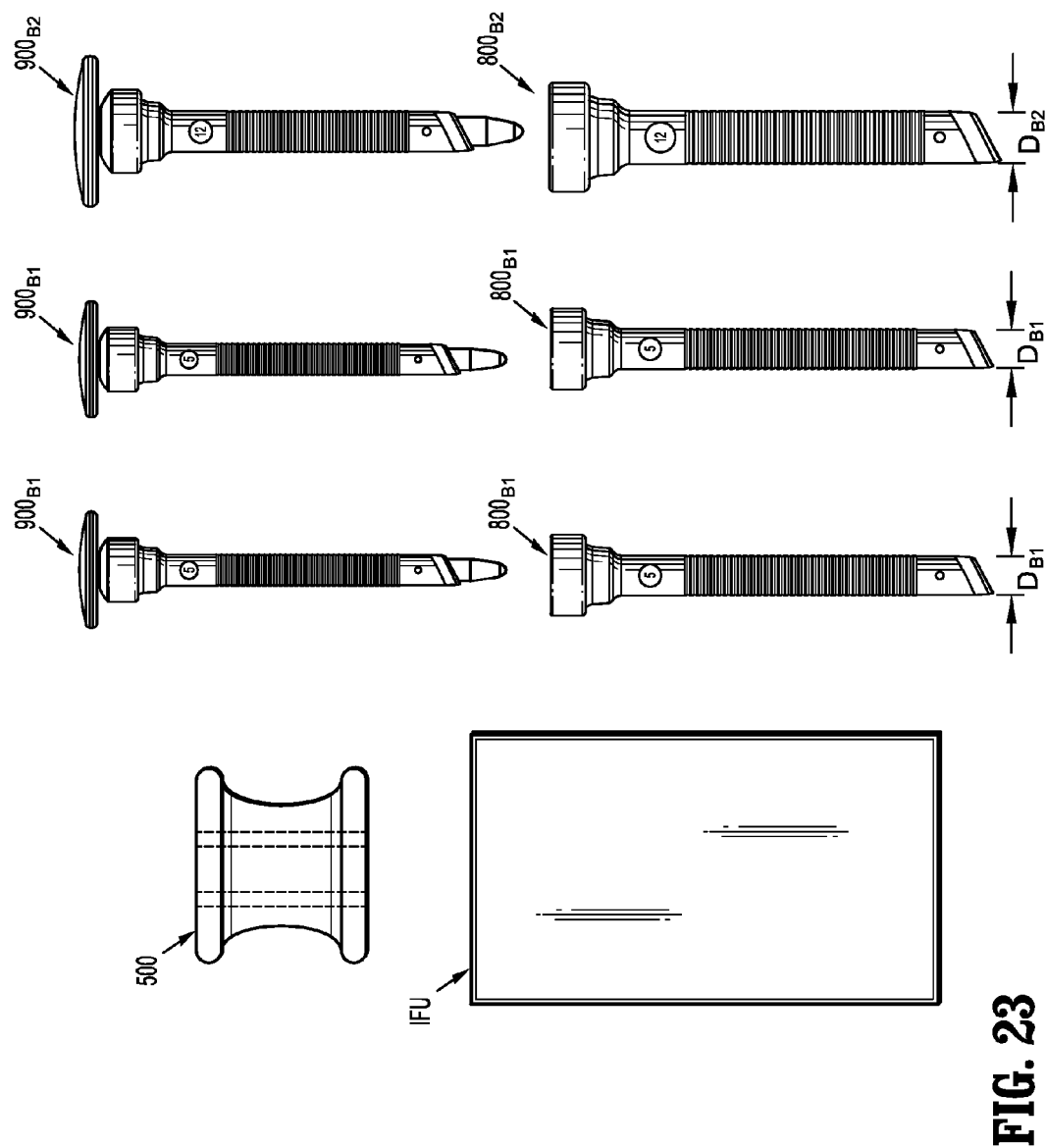
FIG. 23 illustrates an alternate embodiment of the kit of FIG. 22.

With reference now to FIGS. 22-23, kits according to the present disclosure include a seal anchor member, one or more cannulae, and one or more obturators together with instructions for use "IFU". In one embodiment, a first kit 700$_A$ is disclosed that includes the seal anchor member 500 discussed above with respect to FIGS. 19-20, three cannulae 800$_A$ each defining an outer diameter "D$_A$" of 5 mm, and three obturators 900$_A$ configured for removable insertion through the cannulae 800$_A$. In another embodiment, a second kit 700$_B$ is disclosed that includes the seal anchor member 500 discussed above with respect to FIGS. 22-23, two cannulae 800$_{B1}$ each defining an outer diameter "D$_{B1}$" of 5 mm, two obturators 900$_{B1}$ configured for removable insertion through the cannulae 800$_{B1}$, a single cannula 800$_{B2}$ defining an outer diameter "D$_{B2}$" of 12 mm, and a single obturator 900$_{B2}$ configured for removable insertion through the cannulae 800$_{B2}$.

The kit components will typically be maintained within sterile packaging, with individual components being packaged either together or separately in different sterile containers. Usually, even when packaged in separate sterile containers, all components of the kit will be placed together within a common package. The instructions for use "IFU" may be provided on a separate printed sheet, such as a conventional package insert, or may be printed in whole or in part on other portions of the packaging or the device itself.

While the kits 700$_A$, 700$_B$ have been described as including the seal anchor member 500 and three cannulae with corresponding obturators of specific dimensions, it should be understood that kits according to the present disclosure may alternatively include any of the seal anchor members described herein above in combination with any desired number of cannulae and obturators exhibiting any suitable dimensions.

FIGS. 24-26 illustrate another embodiment of the surgical kit. Surgical kit 1000 includes seal anchor member 1100 and fluid delivery, e.g., insufflation/evacuation instrument, 1200 which is positionable within the seal anchor member 1100. Seal anchor member 1100 includes a plurality of passageways 1102 (e.g., four are shown). extending through the seal anchor member 1100, Passageways 1102 may extend in general parallel relation with respect to the longitudinal axis "k". In the alternative, passageways 1102 may be in oblique relation with respect to the longitudinal axis "k" to provide specific directional capability to the seal anchor member 1100. whereby an instrument may be advanced at a predetermined angular orientation relative to the longitudinal axis "k". Passageways 1102 may be radially spaced about the seal anchor member 1100 relative to the longitudinal axis "k". In one aspect, passageways 1102 are spaced a predetermined distance sufficient to correspondingly space the instruments introduced within seal anchor member 1100. This spacing may substantially minimize the potential of engagement of the inserted instruments and enhance freedom of movement above the operative area. Passageways 1102 may be longitudinal bores defined within seal anchor member 1100. Longitudinal bores may be open in an initial or at rest condition. In the alternative, passageways 1102 may define slits or individual valves, e.g. zero closure valves, which are closed in the normal condition in the absence of an object inserted therethrough. In this embodiment, passageways 1102 would open to permit passage of the surgical object. In either case, upon introduction of the surgical object or instrument, the interior surfaces defining passageways 1102 establish a substantial fluid tight seal about the object.

Seal anchor 1100 defines a substantially hourglass configuration and incorporates enlarged leading and trailing flange segments 1104, 1106 to assist in retention within the body cavity. Leading and trailing end faces 1108, 1110 may be recessed as shown and/or may include any number or shape so as to provide improved compressibility of seal anchor 1100 or freedom of movement of any instruments inserted therethrough. Seal anchor 1100 may be fabricated from any of the aforementioned materials including foam, gel or the like.

Insufflation/evacuation instrument 1200 is adapted for positioning within at least one of the passageways 1102. Insufflation/evacuation instrument 1200 may be any suitable instrument adapted to convey fluids or introduce insufflation gases, e.g., $CO_2$ into the peritoneal cavity, and/or evacuate smoke from the cavity. In the depicted embodiment, insufflation instrument 1200 includes housing 1202 and elongated member 1204 extending from the housing 1202. Housing 1202 may be fabricated from any suitable material and incorporates a stop cock valve 1206 to permit selective passage and interruption of fluids, e.g., insufflation gases or smoke therethrough. Housing 1202 includes first and second ports or luer connectors 1208,1210 adjacent stop cock valve 1204. First luer connector 1208 may be adapted for connection to an insufflation source 1212 such as $CO_2$ utilized to insufflate the peritoneal cavity. Second luer connector 1210 may be adapted for fluid connection to an aspiration or gas (e.g. smoke) evacuator 1214. Stop cock valve 1206 may define opening 1216 which is aligned with either port or luer connector 1208, 1210 through selective rotation of the stop cock valve 1206 thereby selectively fluidly connecting the insufflation source 1212 or the evacuator 1214. First and second luer connectors 1208, 1210 may be arranged about axes which are substantially perpendicular to each other. Other orientations are also envisioned.

Elongate member 1204 includes first elongate segment 1216 connected to housing 1202 and second elongate segment 1218 extending contiguously from the first elongate segment 1216. First and second elongate segments 1216, 1218 may be in general alignment with each other. In the alternative, first and second elongate segments 1216, 1218 may be angulated relative to each other at a predetermined angle. In one embodiment, first and second elongate segments 1216, 1218 are arranged at a substantial right angle or perpendicular with respect to each other. This arrangement may facilitate the displacement of housing 1202 and first elongate segment 1216 from the operative area thereby reducing the overall profile of seal anchor member 1100 and insufflation/evacuator instrument 1200. Elongate member 1204 defines a fluid conduit extending through first and second elongate segments 1216, 1218 and in communication with stop cock valve 1206. First and second elongate segments 1216, 1218 may be releasably mounted to each other.

Insufflation/evacuator instrument 1200 may be a separate instrument positionable within one of passageways 1102. In the alternative, seal anchor member 1100 and insufflation/evacuator instrument 1100 may be pre-assembled whereby the insufflation/evacuator instrument 1100 may be permanently connected to the seal anchor member 1100. In one embodiment, second elongate segment 1218 of insufflation/evacuator instrument 1200 includes external anchors 1220a, 1220b mounted about the periphery of the second elongate segment 1218. Anchors 1220a, 1220b may facilitate retention of second elongate segment 1218 of insufflation/evacuation instrument 1200 within seal anchor member 1110. Anchors 1220a, 1220b may be generally annular in configuration or may consist of individual prongs depending outwardly from second elongate segment 1218. Anchors 1220a, 1220b are dimensioned to be embedded within the inner surfaces defining the passageway 1102 accommodating insufflation/evacuation instrument. Trailing anchor 1220a may define an enlarged dimension adjacent its proximal end to resist pull out or retropulsion of insufflation/evacuator instrument 1200. Leading anchor 1220b may define an enlarged dimension adjacent its distal end to prevent over insertion of insufflation/evacuator instrument 1200.

Figure 27:
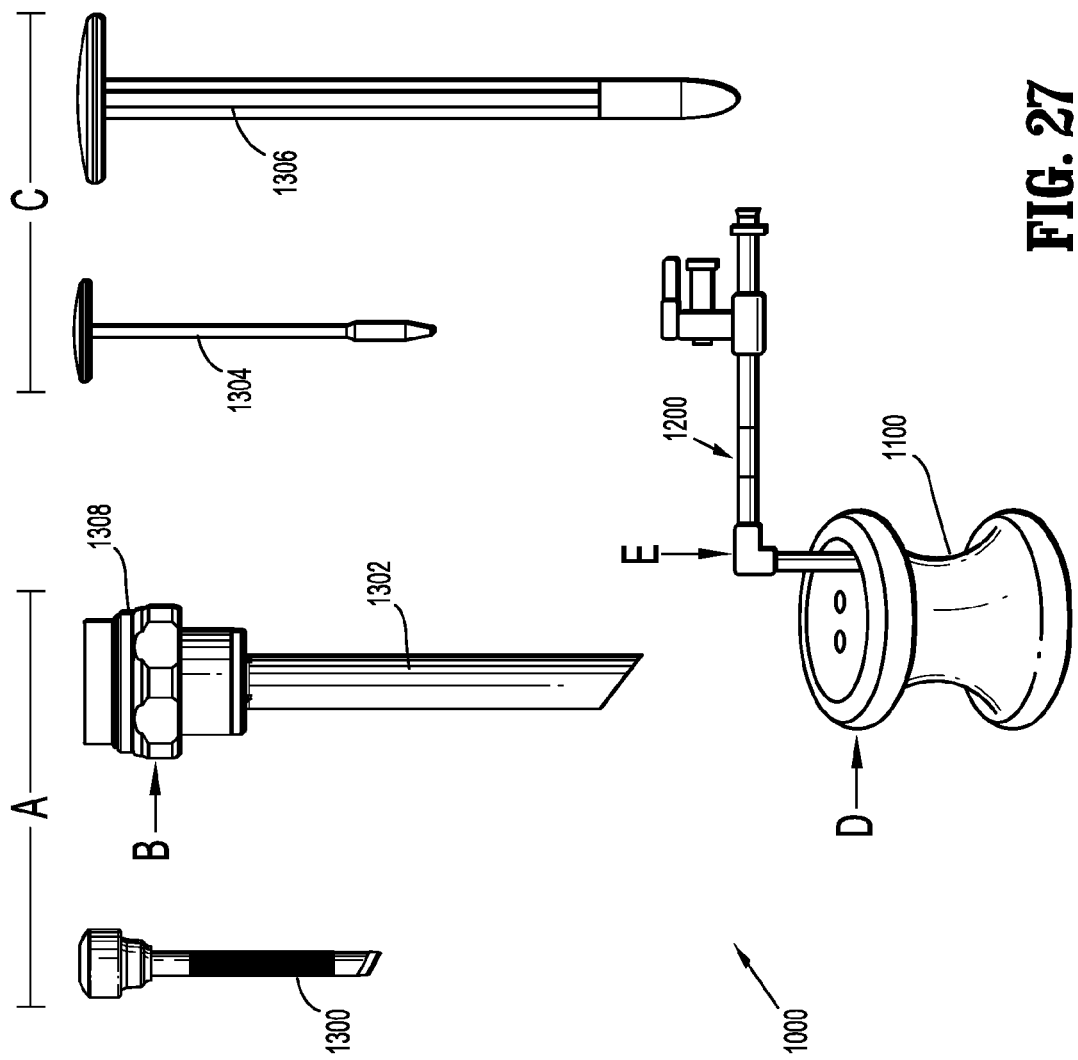
FIG. 27 illustrates additional instrumentation incorporated within the surgical kit of FIGS. 24-26.

Referring now to FIG. 27, additional instrumentation which may be incorporated within surgical kit 1000 is illustrated. Surgical kit 1000 may further include first and second cannulas 1300, 1302 and first and second obturators 1304, 1306 for respective use with the first and second cannulas 1300, 1302. First cannula 1300 may be a 5 mm cannula adapted for reception of instrumentation no greater than 5 mm in diameter. First obturator 1304 is positionable within first cannula 1300 to facilitate advancement of the first cannula 1300 through one of passageways 1102 of seal anchor 1100. Second cannula 1302 may be a 12 mm cannula adapted for reception of instrumentation no greater than 12 mm in diameter and is advanced within seal anchor 1100 with the use of comparably dimensioned second obturator 1306. Second anchor may incorporate a sealing mechanism such as the sealing system disclosed in commonly assigned U.S. Patent Publication No. 2007/0197972 to Racenet, the entire contents of which are hereby incorporated herein by reference. Surgical kit 1000 may incorporate three or more cannulas with corresponding obturators. Any combinations of sizes of cannulas and obturators are envisioned.

Figure 28A:
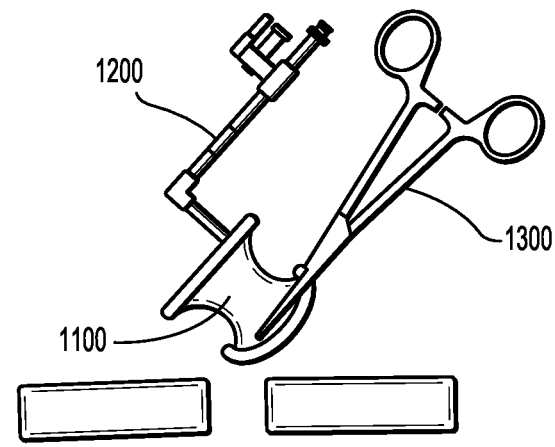
FIGS. 28A-28C illustrate a method of use of the surgical kit of FIGS. 24-27.
Figure 28B:
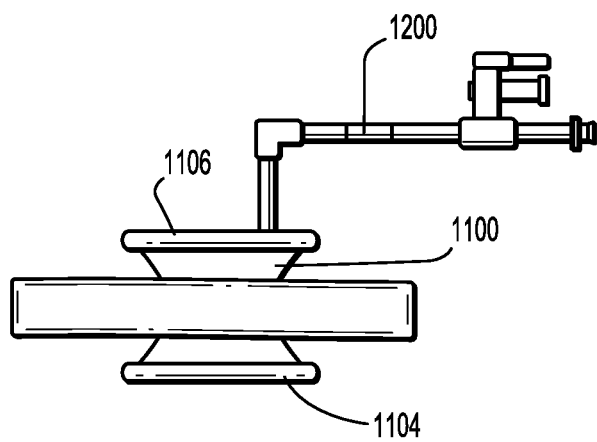
Figure 28C:
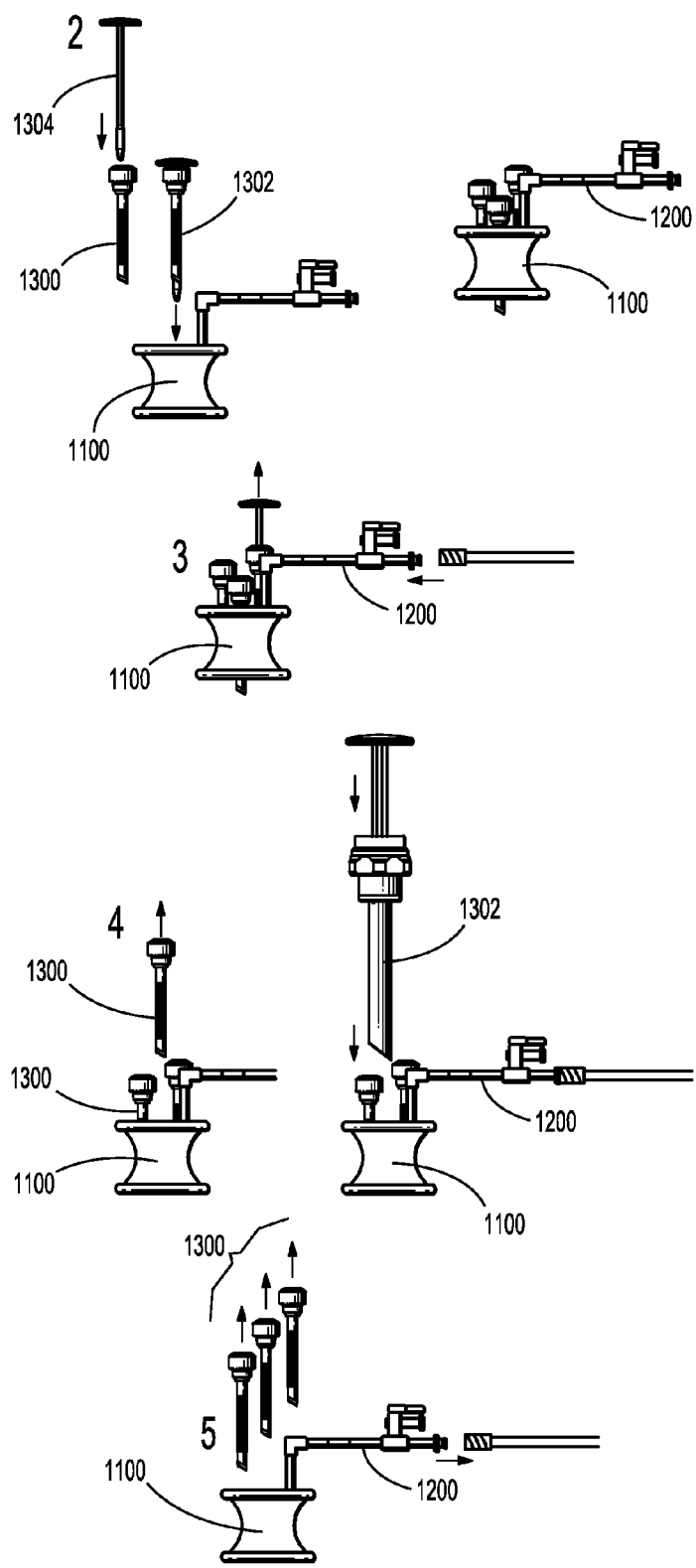

FIGS. 28A-28C disclose a method of use of surgical kit. An incision is made in the tissue, e.g., the abdominal tissue, and blunt dissection through the facia and peritoneum is achieved through known methods. Leading flange and end face 1104, 1108 of seal anchor 1100 are manipulated within the incision (FIG. 28A), possibly, with the assistance of a surgical clamp 1400. When appropriately positioned within incision, seal anchor 1100 snugly engages the interior surfaces of the incision with leading and trailing flanges 1104, 1106 adjacent the abdominal lining and outer dermal tissue, respectively (FIG. 28B). Thereafter, any combinations of cannulas 1300, 1302 may be introduced within passageways 1102 of seal anchor 1100 with the use of corresponding obturators 1304, 1306. (FIG. 28C) Upon positioning, the obturators are removed thereby providing access through the appropriate cannula 1300, 1302 for passage of surgical instrumentation to perform the surgical procedure. Cannulas 1300, 1302 may be staggered relative to seal anchor 1100 to facilitate freedom of movement above the operative area. Removal of one cannula 1300, 1302 and replacement with another sized cannula 1300, 1302 may be readily achieved. In the event, passageways 1102 of seal anchor 1100 are open in the initial condition (e.g., in the absence of an instrument), the surgeon may place a finger over the passageway upon removal of the cannula and remove the finger when introducing the second cannula within the passageway. Insufflation and/or evacuation may be continuously effected throughout the procedure with the use of stock cock valve 1204.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical kit positionable within a tissue tract comprising:
    a seal anchor member transitionable between a first state defining a first diameter and a second state defining a second diameter that is different from the first diameter, the seal anchor member being adapted for insertion within the tissue tract when in the first state and forming a substantially sealed relationship with the tissue tract as the seal anchor member resiliently transitions towards the second state, the seal anchor member having opposing leading and trailing ends defining a longitudinal axis of the seal anchor member, at least one of the opposing leading and trailing ends having a concave configuration;
    at least one port extending longitudinally through the seal anchor member, the at least one port adapted for reception of an object therethrough, the at least one port resiliently deforming as the object is translated distally through the at least one port and conforming about the object for forming a substantially sealed relationship therewith; and
    a fluid conveying instrument including an elongate segment positioned within the at least one port, and a peripheral anchor configured to facilitate retention of the elongate segment within the at least one port, the peripheral anchor extending radially outward from the elongate segment.

2. The surgical kit according to claim 1 wherein each of the leading and trailing ends exhibit an arcuate configuration.

3. The surgical kit according to claim 1 wherein the seal anchor member is formed of a foam material.

4. The surgical kit according to claim 3 wherein the foam material is at least partially constituted of a material selected from the group consisting of: polyisoprene, urethane, and silicone.

5. The surgical kit according to claim 1 wherein the seal anchor member is formed of a gel material.

6. The surgical kit according to claim 1 wherein the at least one port includes a plurality of longitudinal ports.

7. The surgical kit according to claim 6 wherein the plurality of longitudinal ports are configured symmetrically with respect to the longitudinal axis.

8. The surgical kit according to claim 6 wherein the plurality of longitudinal ports are spaced equidistant from the longitudinal axis.

9. The surgical kit according to claim 6 wherein the plurality of longitudinal ports are spaced equally from one another.

10. The surgical kit according to claim 1 wherein the fluid conveying instrument is adapted to introduce insufflation gases to an underlying body cavity and evacuate gases from the underlying cavity.

11. The surgical kit according to claim 1 wherein the fluid conveying instrument includes a stop cock valve.

12. The surgical access kit according to claim 11 wherein the stop cock valve includes first and second ports for fluid coupling to an insufflation instrument and an evacuator, the stock cock valve further defining an opening, the stop cock valve being selectively movable to align the opening with either of the first and second ports.

13. The surgical kit according to claim 6 including at least one cannula positionable within one longitudinal port of the plurality of longitudinal ports of the seal anchor member.

14. The surgical kit according to claim 13 including a plurality of cannulas, each cannula of the plurality of cannulas positionable within one longitudinal port of the plurality of longitudinal ports of the seal anchor member.

15. The surgical kit according to claim 1 wherein the peripheral anchor of the fluid conveying instrument has an annular configuration.

16. The surgical kit according to claim 1 wherein the peripheral anchor of the fluid conveying instrument includes a plurality of prongs depending outwardly from the elongate segment.

* * * * *